(12) United States Patent
Sekura et al.

(10) Patent No.: US 6,198,383 B1
(45) Date of Patent: *Mar. 6, 2001

(54) PRESCRIPTION COMPLIANCE DEVICE AND METHOD OF USING DEVICE

(76) Inventors: Ronald D. Sekura; Carol M. Sekura, both of 100 Anchor Dr. #431, Key Largo, FL (US) 33037

(*) Notice: Subject to any disclaimer, the term of this patent is extended or adjusted under 35 U.S.C. 154(b) by 0 days.

This patent is subject to a terminal disclaimer.

(21) Appl. No.: 09/425,292

(22) Filed: Oct. 25, 1999

Related U.S. Application Data

(63) Continuation of application No. 08/990,811, filed on Dec. 15, 1997, now Pat. No. 6,018,289, which is a continuation-in-part of application No. PCT/US96/09241, filed on Jun. 14, 1996.
(60) Provisional application No. 60/000,232, filed on Jun. 15, 1995, and provisional application No. 60/044,265, filed on Apr. 25, 1997.

(51) Int. Cl.[7] .................................................. G08B 1/00
(52) U.S. Cl. ............................. 340/309.4; 221/2; 221/3; 221/15; 368/10
(58) Field of Search ........................... 340/309.4, 309.15; 221/2, 3, 15; 368/10

(56) References Cited

U.S. PATENT DOCUMENTS

| | | |
|---|---|---|
| 4,293,845 | 10/1981 | Villa-Real . |
| 4,302,752 | 11/1981 | Weitzler . |
| 4,361,408 * | 11/1982 | Wirtschafter ...................... 340/309.4 |
| 4,419,016 | 12/1983 | Zoltan . |
| 4,448,541 | 5/1984 | Wirtschafter . |
| 4,504,153 | 3/1985 | Schollmeyer . |
| 4,617,557 | 10/1986 | Gordon . |
| 4,626,105 | 12/1986 | Miller . |
| 4,695,954 | 9/1987 | Rose et al. . |
| 4,768,176 | 8/1988 | Kehr et al. . |
| 4,798,309 | 1/1989 | Stone et al. . |
| 4,849,948 | 7/1989 | Davis et al. . |
| 4,942,544 * | 7/1990 | McIntosh et al. ................. 340/309.4 |
| 5,020,037 | 5/1991 | Raven . |
| 5,050,037 | 9/1991 | Yamamoto et al. . |
| 5,088,056 | 2/1992 | McIntosh et al. . |
| 5,099,463 | 3/1992 | Lloyd et al. . |
| 5,157,640 | 10/1992 | Backner . |
| 5,170,380 | 12/1992 | Howard et al. . |
| 5,200,891 | 4/1993 | Kehr et al. . |
| 5,239,491 | 8/1993 | Mucciacciaro . |

(List continued on next page.)

*Primary Examiner*—Jeffery A. Hofsass
*Assistant Examiner*—John Tweel, Jr.
(74) *Attorney, Agent, or Firm*—Oblon, Spivak, McClelland, Maier & Neustadt, P.C.

(57) ABSTRACT

A prescription compliance device which aids patients in complying with instructions given by a physician for taking prescription medication. The device reminds a patient when the next dose of medication is to the taken and indicates whether a specified dose has been taken. The device includes a microcontroller, a display, a program memory for storing pre-programmed medication-taking regimens for single and multiple medications, a real time clock, a selector for selecting one of the regimens and for programming the device as to the time and day on which a first dose of medication is to be taken, a display which alternately displays the current time and a time at which a next dose of medication is to be taken, and an alarm which alerts the patient at times when a dose of medication is to be taken. The selector includes an event switch which is activated by the patient after taking a dose of medication so as to record the taking of the medication and to cause the microcontroller to effect the display of the next time at which a dose of medication is to be taken. A memory may also be included to record the times at which a patient takes doses of medication. The device is small enough to be attached to medication containers, and includes a remote programming feature via a wireless link.

40 Claims, 20 Drawing Sheets

U.S. PATENT DOCUMENTS

| | | |
|---|---|---|
| 5,289,157 | 2/1994 | Rudick et al. . |
| 5,337,919 | 8/1994 | Spaulding et al. . |
| 5,347,453 | 9/1994 | Maestre . |
| 5,408,443 * | 4/1995 | Weinberger ............................... 221/3 |
| 5,412,372 | 5/1995 | Parkhurst et al. . |
| 5,495,961 * | 3/1996 | Maestre ................................... 221/3 |
| 5,554,967 * | 9/1996 | Cook et al. ...................... 340/309.4 |
| 5,583,831 | 12/1996 | Churchill et al. . |
| 5,625,334 * | 4/1997 | Compton ........................... 340/309.4 |
| 5,710,551 | 1/1998 | Ridgeway . |
| 5,724,021 | 3/1998 | Perrone . |
| 5,805,051 * | 9/1998 | Herrmann et al. ................ 340/309.4 |
| 6,018,289 * | 1/2000 | Sekura et al. ..................... 340/309.4 |

\* cited by examiner

FIG. 4

| REGIMEN NO. | INTERVAL |
|---|---|
| 0 | EVERY 24 HRS. ; ONCE DAILY |
| 1 | B,D  ⎫ |
| 2 | B,L,D  ⎬ WITH MEALS |
| 3 | B,L,D,N  ⎭ |
| 4 | EVERY 48 HRS. ; EVERY OTHER DAY |
| 5 | EVERY 6 HRS. ; 4 TIMES DAILY |
| 6 | EVERY 4 HRS. ; 6 TIMES DAILY |
| 7 | EVERY 8 HRS. ; 3 TIMES DAILY |
| 8 | EVERY 12 HRS. ; 2 TIMES DAILY |

B=BREAKFAST
L=LUNCH
D=DINNER
N=BEDTIME

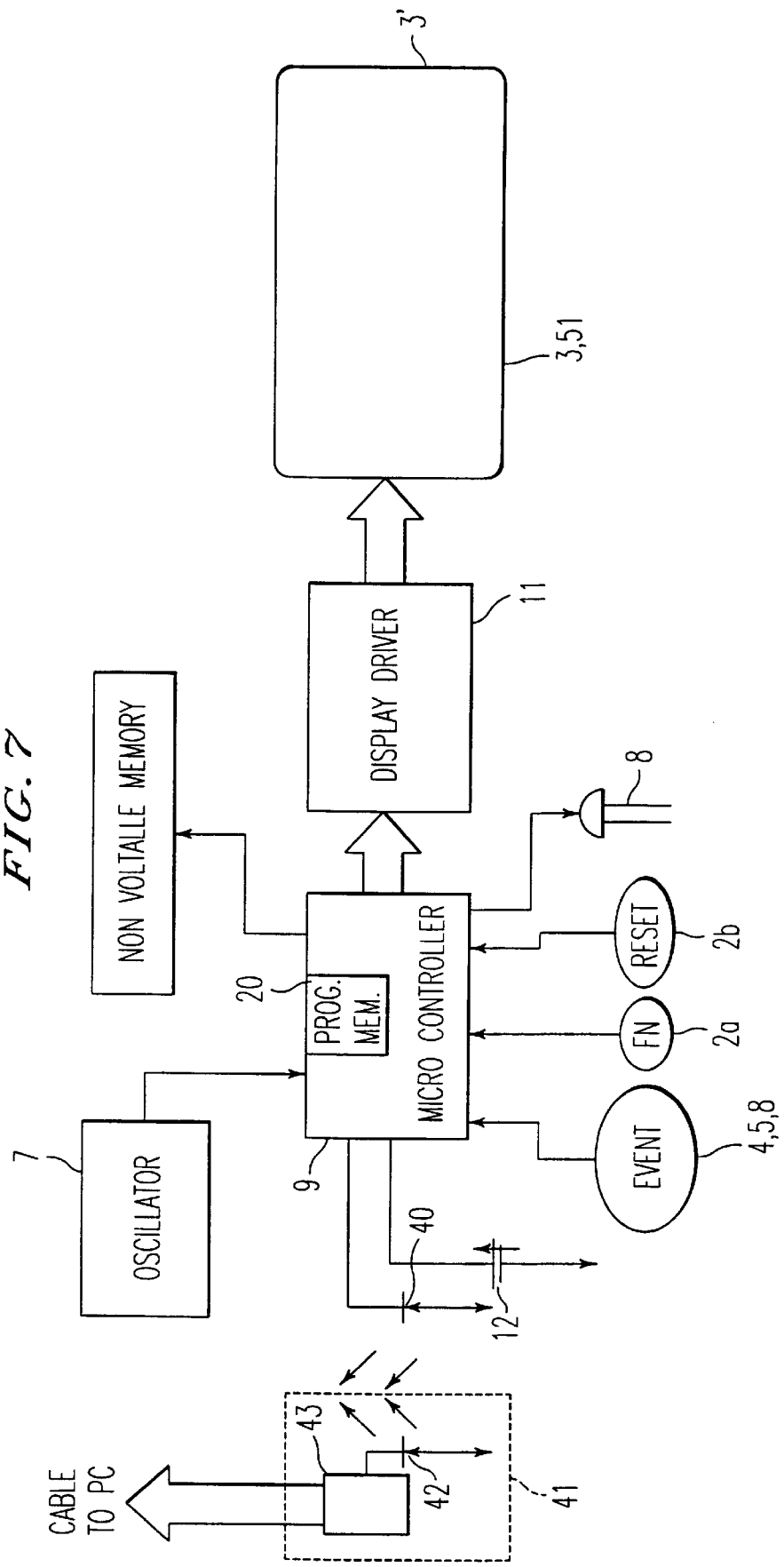

FIG. 9

| REG# | PRESCRIBED REG. | DOSAGE TIMES | RANGE |
|---|---|---|---|
| 0 | CUSTOM | 1 PATIENT SPECIFIED | +/-1 Hr |
| 1 | QD. QAM. QPM. QHS. ONCE A DAY. ONCE EVERY 24 Hr | 1st | +/-4 Hr |
| 2 | BID. TWICE A DAY | 1st, AND 5th | +/-3 Hr |
| 3 | TID. THREE TIMES A DAY | 1st, 3rd AND 6th | +/-2 Hr |
| 4 | QID. FOUR TIMES A DAY | 1st, 2nd, 4th, AND 6th | +/-1 Hr |
| 5 | QXXH. TAKE EVERY Hr | INTERVALS CALCULATED ON BASIS OF XX | +/-0.25XX OR 4 Hr |
| 6 | PRN. XXHr. TAKE AS NEEDED EVERY XX Hr | LAST DOSE (OR INITIAL DOSE) +XX | NONE |
| 7 | DAYS IN CYCLE | 1st | +/-4 Hr |
| 8 | MEALS | DEFAULT OR SET | +/-1 Hr |
| 9 | AFTER MEALS | DEFAULT OF SET TIMES +2 Hr | +/-1 Hr |
| 10 | BEFORE MEALS | DEFAULT OR SET TIMES - 1 Hr | +/-Hr |
| 11 | RECORD ONLY | | | ion compliance device that maintains a count of the number of doses remaining in a patient's prescription and displays the count so that a patient will know when to have the prescription refilled.

PRESCRIPTION COMPLIANCE DEVICE AND METHOD OF USING DEVICE

CROSS-REFERENCES TO RELATED APPLICATIONS

This is a Continuation of U.S. patent application Ser. No. 08/990,811 filed Dec. 15, 1997, now U.S. Pat. No. 6,018, 289, which is a Continuation-in-Part application of the International Application Ser. No. PCT/US96/09241 filed Jun. 14, 1996 which is incorporated herein by reference. In addition, full benefit of the filing date of U.S. Provisional Application Ser. No. 60/000,232 filed Jun. 15, 1995, International Application Ser. No. PCT/US96/09241 filed Jun. 14, 1996, and U.S. Provisional Application Ser. No. 60/044, 265 filed Apr. 25, 1997 are claimed pursuant to the provisions of 35 U.S.C. §119(e), and are incorporated herein by reference.

BACKGROUND OF THE INVENTION

1. Field of the Invention

This invention relates to an apparatus which aids patients in complying with instructions given by a physician for taking prescription medication, and more particularly, to a device which is programmable in accordance with the physician's instructions or desired regimen.

2. Discussion of the Background Art

A variety of devices have been proposed for recording intervals at which patients, especially those under the care of an attendant, take medication at periodic intervals prescribed by a physician. If the patient or his medical care provider ignores the proper instructions and repeats the dose too frequently or fails to administer or take medication at the proper time, the concentration of medication in the patient's body may become too high or too low. In order to ensure that medications are taken at the proper time, a variety of devices, such as the one disclosed in U.S. Pat. No. 4,361, 408, have been devised to generate audible and/or visible prompting or alarm signals that remind a patient or his caretaker to administer the correct dosages at the correct time. Such devices have been complex and costly, inconvenient to program, and have not been flexible enough in establishing varying time intervals at which the medication needs to be administered.

SUMMARY OF THE INVENTION

Accordingly, one object of this invention is to provide a low cost, easy to use prescription compliance device that has the flexibility of operating in accordance with various different medication-taking intervals.

Another object of this invention is to provide a prescription compliance device which is easily programmable either by activating a programmer on the device itself or by remotely programming the device via a wireless link. Multiple programming regimens which correspond to different medication-taking intervals and medication-types may also be programmed into the device.

Yet another object of this invention is to provide a prescription compliance device which records the event of taking a dose of medication and displays the time at which the next dose of medication is to be taken.

A still further object of this invention is to provide a prescription compliance device having a timer which measures the time that has elapsed since the patient last took a dose of the medication and an alarm which is activated at times when the patient is to take the next dose of medication.

A further object of this invention is to provide a prescription compliance device that maintains a count of the number of doses remaining in a patient's prescription and displays the count so that a patient will know when to have the prescription refilled.

Another object of this invention is to provide a prescription compliance device that alerts a patient when the patient has missed a scheduled dose of medication or has taken a dose of medication at a non-scheduled time.

Yet another object of this invention is to provide a prescription compliance device which records the times at which a patient takes each dose of medication in a format that can be easily accessed via a wireless interface.

These and other objects are accomplished by a prescription compliance device which includes a microcontroller, a program memory which stores data representing a plurality of pre-programmed medication-taking regimens for single and multiple medications, an oscillator which controls timing functions of the device, a selector selecting one of the regimens and programming the device in accordance with the selected regimen, a display which alternately displays the current time, the time at which a next dose of medication is to be taken in accordance with the regimen selected by the selector, and the number of doses remaining in a prescription, and an alarm which alerts the patient at times when the patient is scheduled to take a dose of medication. The device may also include a memory which records the times at which a patient takes each dose of medication in a format that can be easily accessed via a wireless interface.

The selector includes an event switch which is activated by the patient after taking a dose of medication to record the taking of the medication, the event switch causing the microcontroller to effect the display of the next time at which a dose of the medication is scheduled to be taken, in accordance with the regimen selected by the selector.

The event switch and a function button are provided for programming the regimens by which the medication is to be taken, the day o the week on which the first dose is to be taken, the time at which the first dose is to be taken or the designation of meals during which the first dose is to be taken, and the number of doses in a patient's prescription.

Programming may be done either directly by using the function button and the event switch or remotely via a wireless link. To program from a remote location, the device is provided with a wireless transmitter/receiver and an external wireless transmitter/receiver configured to be connected to an input device. The external wireless transmitter/receiver communicates with the wireless transmitter/receiver via a wireless link to select one of the regimens and to program the device in accordance with the selected regimen.

The display includes a first display area which displays a number of the regimen selected by the selector, a second display area which may alternately display the current day of the week and a day of the week on which a next dose of medication is to be taken, a third display area which alternately displays the current time, the time or meal at which the next dose of medication is to be taken and the number of doses remaining in a prescription, a fourth display area which alternately displays AM or PM designations for the current time and the time at which a next dose of medication is to be taken, and a fifth display area which displays an icon indicating the nature of the information currently displayed in the first through fourth display areas.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a table listing examples of common medication-taking regimens which may be programmed into the prescription compliance device;

FIG. 7 is a block diagram of a prescription compliance device including a memory for recording the takings of medication and wireless programming capabilities;

FIG. 9 is another table listing examples of common medication-taken regimens which may be programmed into the prescription compliance device.

DESCRIPTION OF THE PREFERRED EMBODIMENTS

Figure 1:
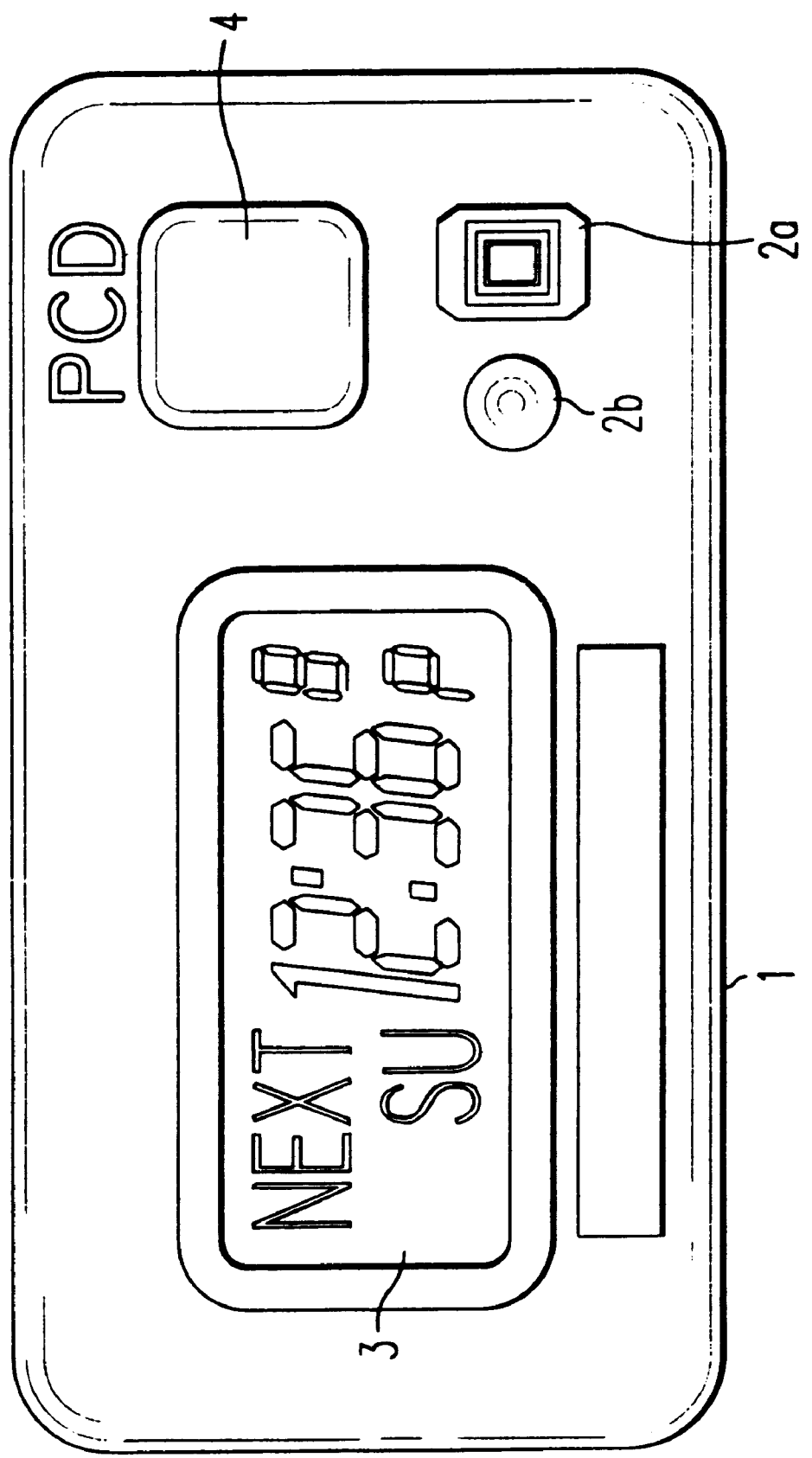
FIG. 1 is an illustration of a prescription compliance device in accordance with a first embodiment of the present invention.

Referring now to the drawings, wherein like reference numerals designate identical or corresponding parts throughout the several views, and more particularly to FIG. 1 thereof, a prescription compliance device 1 according to a first embodiment of the present invention includes a function button 2a, a reset button 2b, and an event switch 4 for programming the device, and a display 3 for displaying the programmed information. The event switch 4 is activated by the patient upon the taking of a dose of medication.

Prescription Compliance Device For Single Medications

Figure 2:
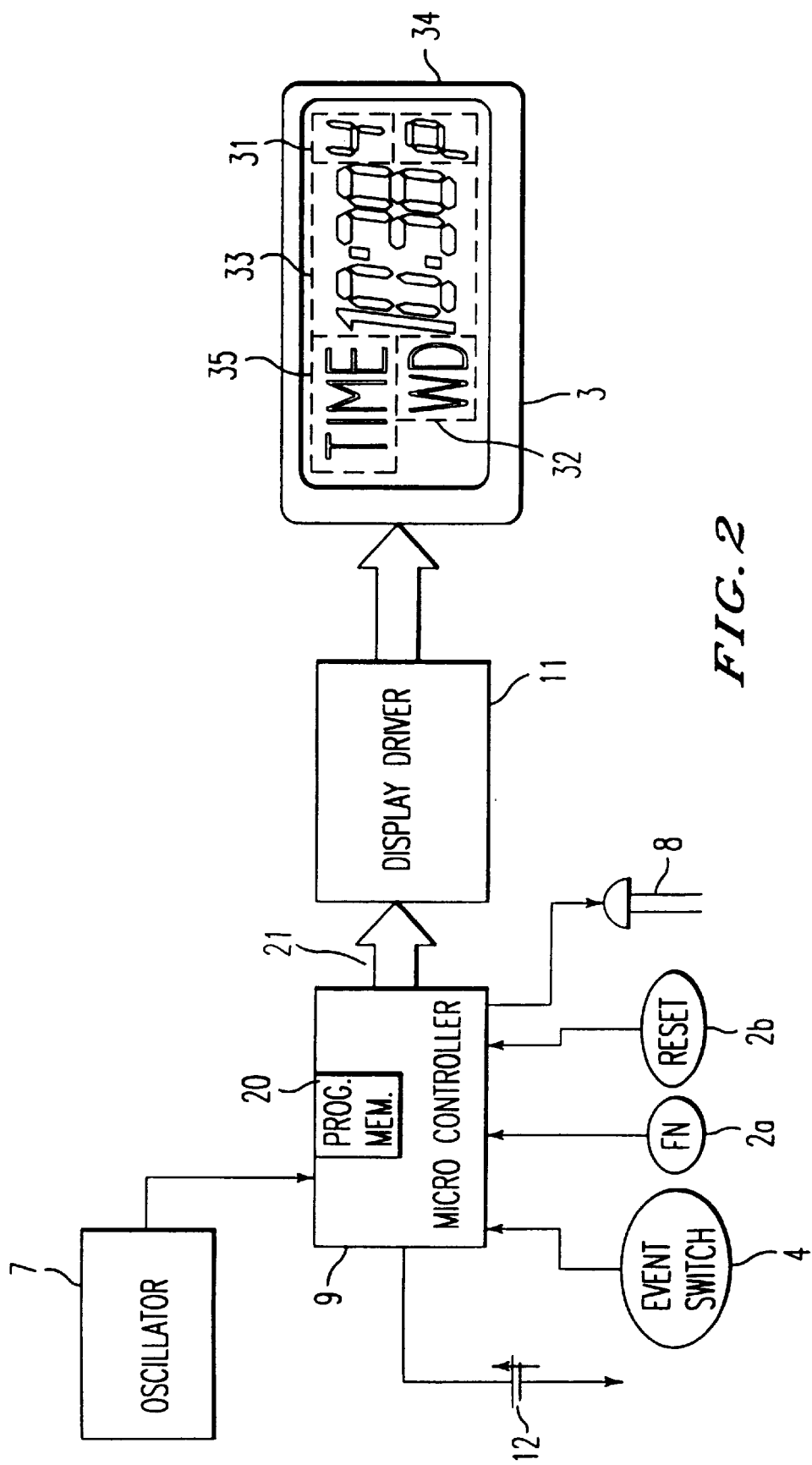
FIG. 2 is a block diagram of a prescription compliance device of FIG. 1.
Figure 3A:
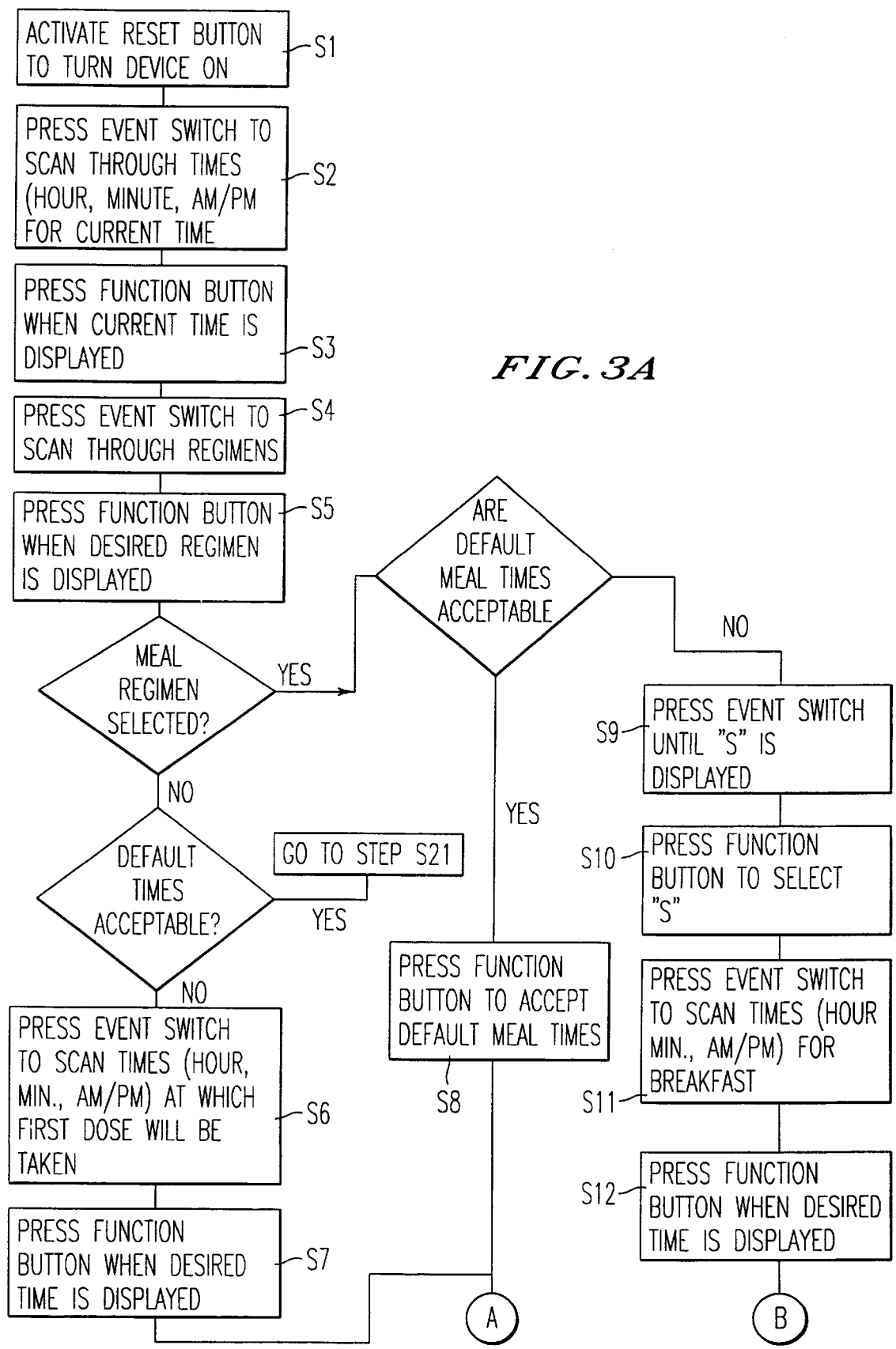
FIGS. 3A–3E are flow diagrams illustrating the steps followed when operating the prescription compliance device.
Figure 3B:
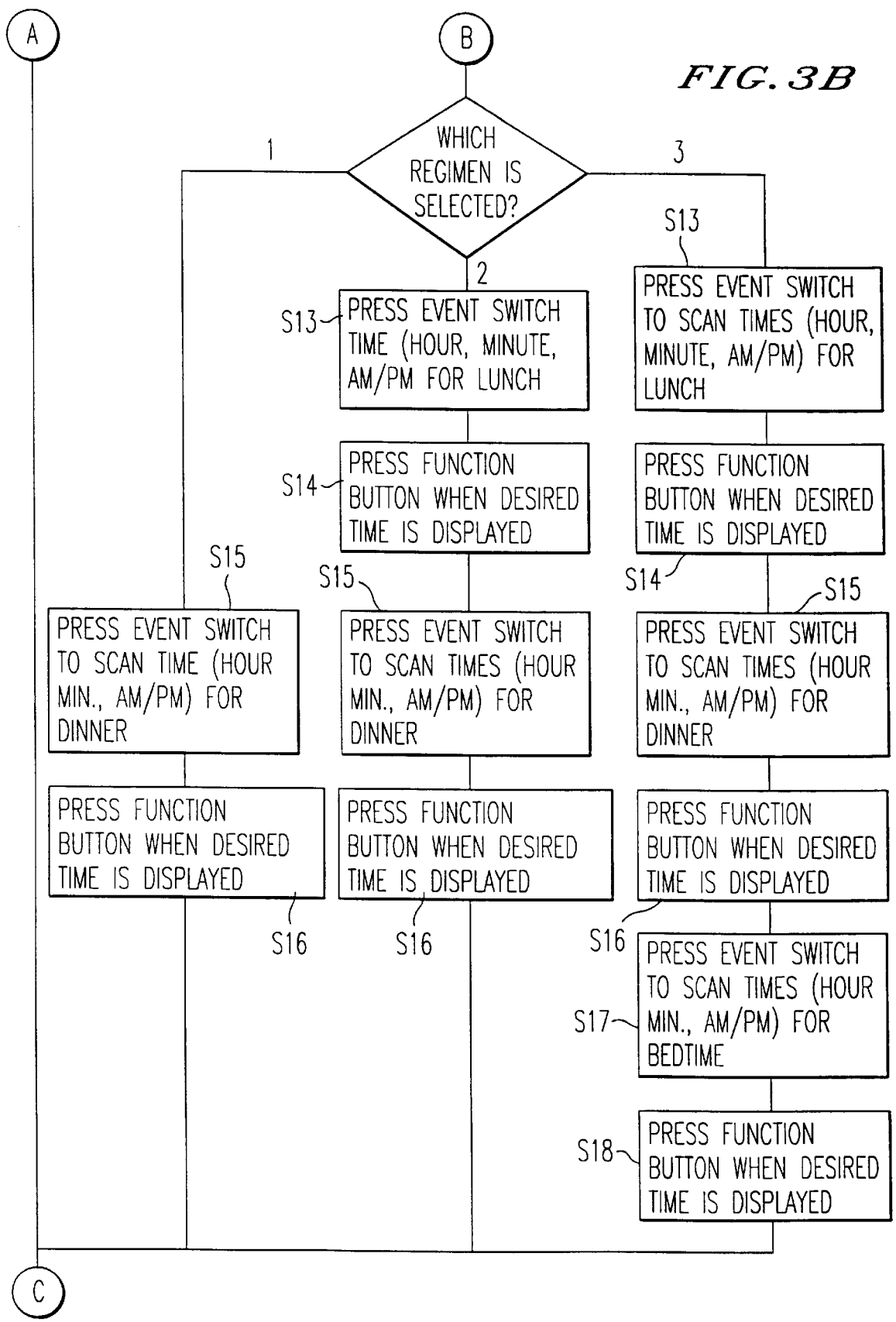
Figure 3C:
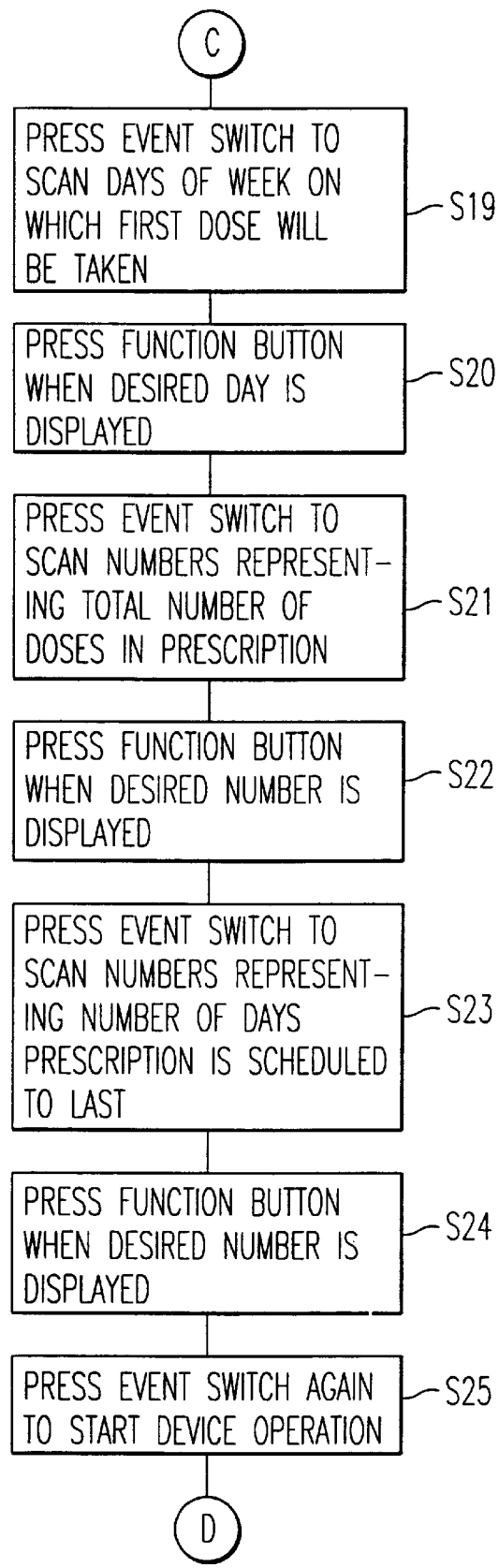
Figure 3D:
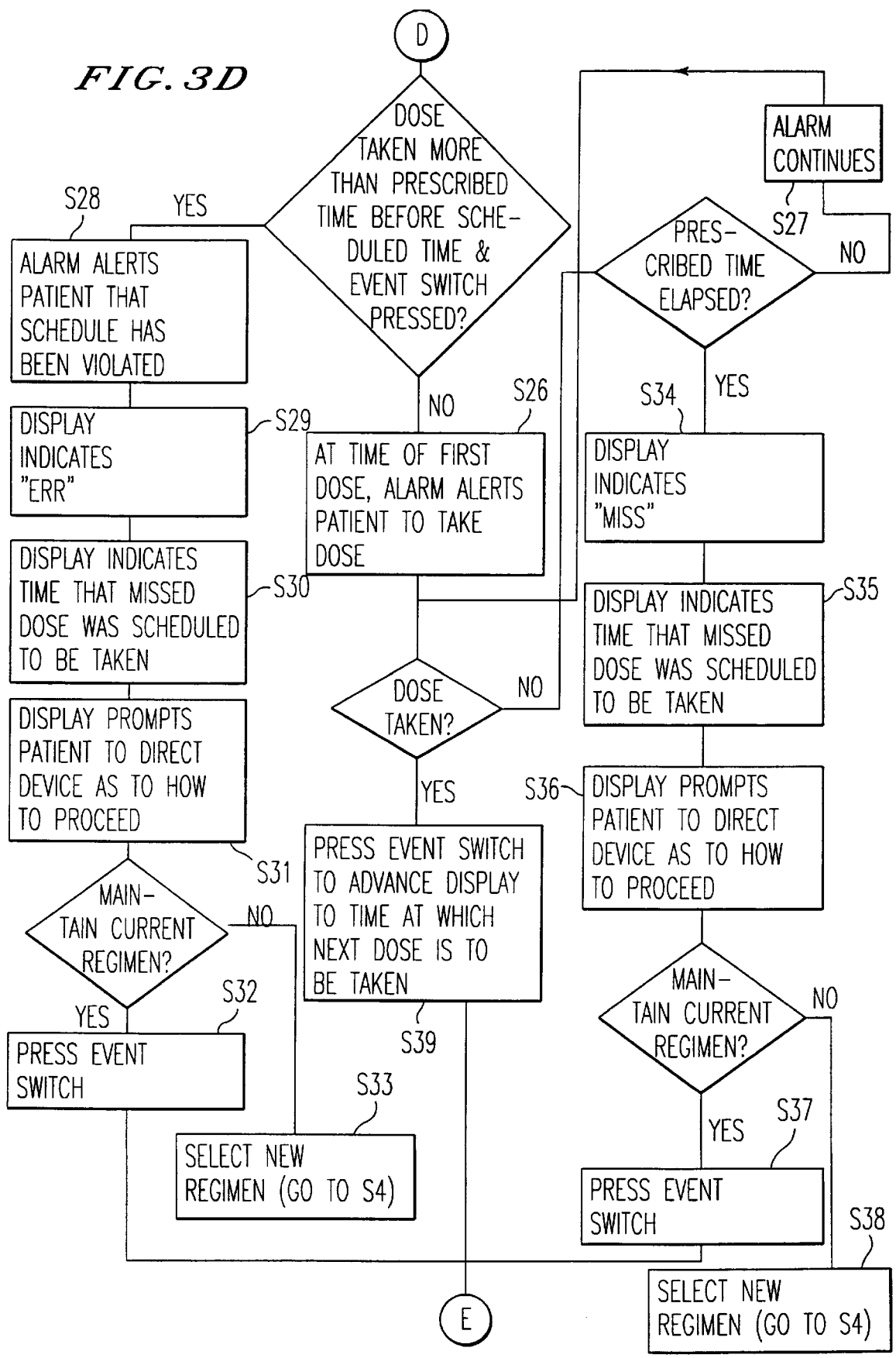
Figure 3E:
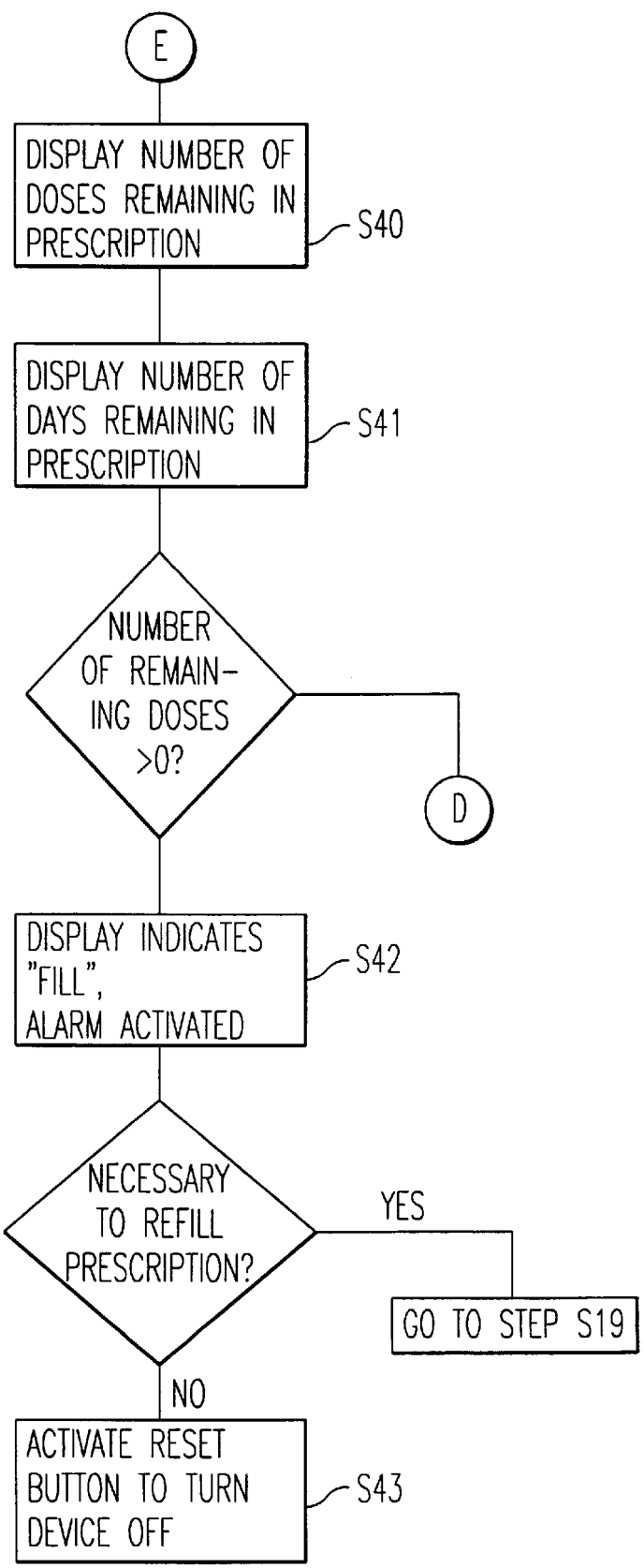

FIG. 2 illustrates a block diagram of the prescription compliance device according to the first embodiment of the invention. The illustrated and described configuration is exemplary and any desired hardware implementation can be used. An 8-bit microcontroller 9 such as Microchip Part No. PIC 16C954, for example which controls the overall functions of the device includes a program memory 20 for storing preprogrammed medication-taking regimens. A 32 KHz crystal oscillator 7 controls all timings of the device. The program memory 20 is preferably a dedicated chip mask read only memory (ROM), although other nonvolatile memories such as a flash memory or EEPROM may be used. The specific parameters of the microcontroller, program memory, and the oscillator are set forth here solely for illustrative purposes and are not intended to limit the scope of the invention. The use of equivalent elements is contemplated within the scope of this invention.

The microcontroller receives inputs from the function and reset buttons 2a, 2b and from the event switch 4 and controls the device functions in accordance with the pre-programmed regimens stored in program memory 20. The microcontroller 9 is connected via an 8-bit bus 21 to display driver 11 which drives the display 3 to display relevant information in display areas 31–35. The display 3 is preferably a liquid crystal display (LCD) and the display driver 11 an ASIC LCD driver. Battery 12 is preferably a 3 volt battery and alarm circuit 8 may visually and/or audibly prompt the patient to take medication. However, equivalents are also within the scope of the invention.

The operation of the prescription compliance device according to this embodiment of this invention will now be described with reference to FIGS. 3A–3E. Patients who are under the care of an attendant are instructed to take medication at periodic intervals as prescribed by a physician. Upon receiving the prescription, the patient or his medical care provider employs the prescription compliance device to aid the patient in complying with the instructions given by the physician.

First, the device must be switched from an OFF state to an ON state by pressing the reset button (Step SI). A "SET" icon is displayed in display area 35 to indicate that the device is in a setup mode. The patient first sets the current time (Steps S2 and S3) as follows.

The event switch 4 is pressed and the microcontroller 9 directs the display area 33 to blink hour digits "12". Hours "1" through "12" are scanned through by pressing the event switch 4 and the appropriate hour is selected by pressing the function button 2a when that hour is displayed.

The minutes tenth digit then blinks "0" and the digits "0" through "5" are scanned through by pressing the event switch 4. The appropriate digit is selected by pressing the function button 2a when that digit is displayed.

The minutes unit digit then blinks "0" and the digits "0" through "9", are scanned through by pressing the event switch 4. The appropriate digit is selected by pressing the function button 2a when that digit is displayed.

The display area 34 then blinks "A" and the patient selects AM or PM time designations using the event switch 4 to toggle between the two and the function button 2a to select. This completes the setting of the current time.

The patient now selects the regimen by which the prescription medication is to be taken. Upon depressing the event switch 4, the display area 35 displays "RGMN" and the display area 31 blinks "0", prompting the patient to scan through and select a desired regimen using the event switch 4 (Step S4). FIG. 4 lists examples of common programming regimens which may be pre-programmed into program memory 20. These regimens are listed only by way of example and other regimens are possible.

In FIG. 4, regimens are provided for taking the medication 1, 2, 3, 4, or 6 times daily, taking the medication with breakfast and dinner, with breakfast, lunch, and dinner, or with breakfast, lunch, dinner, and at bedtime, and for taking the medication once every 48 hours.

The patient presses the event switch 4 to advance through the programming regimens. During scanning, regimen numbers appear in display area 31 and descriptions of the regimens appear in display area 35 so that the patient knows which regimen each number corresponds to. For example, when "8" appears in display area 31, "3:D" appears in display area 35 to indicate to the patient that programming regimen 8 corresponds to taking medication three times daily.

When the desired regimen is displayed, the function key 2a is pressed (Step S5) and the display 3 prompts the patient to choose between standard, pre-programmed default times corresponding to the selected regimen or setting a specific time at which the first dose is to be taken. If the default times for taking the medication are acceptable, the patient presses the event switch 4 and is then prompted to enter the number of doses in the prescription (Step S21).

If the patient instead wants to set the time at which the first dose is to be taken, the microcontroller 9 directs the display area 33 to blink hour digits "12". Unless the patient selects one of the meal regimens, the time of day at which the first dose of the medication is to be taken is next programmed (Steps S6 and S7). Hours "1" through "12" are scanned through by pressing the event switch 4 and the appropriate hour is selected by pressing the function button 2a when that hour is displayed.

The minutes tenth digit then blinks "0" and the digits "0" through "5" are scanned through by pressing the event switch 4. The appropriate digit is selected by pressing the function button 2a when that digit is displayed.

The minutes unit digit then blinks "0" and the digits "0" through "9" are scanned through by pressing the event switch 4. The appropriate digit is selected by pressing the function button 2a when that digit is displayed.

The display area 34 then blinks "A" and the patient selects AM or PM time designations using the event switch 4 to toggle between the two and the function button 2a to select. This completes the setting of the time at which a first dose of medication is to be taken by the patient.

If one of the meal regimens is selected, the medication is to be taken with meals the times of which will vary from person to person. The program memory 20 has pre-programmed therein standard meal times (breakfast, lunch, dinner) during which most persons normally eat. However, the device is flexible enough to allow for different meal times, as will now be explained.

After a meal regimen is selected, display area 33 blinks "D" for default meal times. If the patient eats meals at the standard times programmed into the program memory 20, then the function button 2a is pressed when "D" is displayed (Step S8). If the patient eats at different times, then pressing the event switch 4 (Step S9) allows the patient to toggle between "D" and "S" (indicating 'set'). Pressing the function key 2a when "S" is displayed (Step S10) allows the user to set his breakfast, lunch, dinner, and bedtimes as follows. After the function key 2a is pressed, "BRKF" appears in display area 35 and "12" blinks in display area 33. The patient's breakfast time (hour, minute, AM/PM) is entered as described above (Steps S11 and S12).

After programming the breakfast time, the operation varies according to the specific regimen selected. For explanatory purposes, regimens 1, 2, and 3 refer to the meal designations listed in FIG. 4. If regimen 2 or 3 has been selected, "LNCH" appears in display area 35 and the time setting process is repeated to set the patient's lunch time (Steps S13 and S14). "DINR" then appears in display area 35 under regimens 1, 2, and 3 and the patient's dinner time is similarly set (Steps S15 and S16). Finally, "BDTM" appears in display area 35 if regimen 3 is selected and the patient's bedtime is set as described above (Steps S17 and S18).

Once the time/meal designations have been programmed, the display area 32 then blinks "SU", prompting the patient to program the day of the week on which the first dose is to be taken. The days "SU" through "SA" are scanned through by pressing the event switch 4 (Step S19) and the appropriate day is selected by pressing the function button 2a (Step S20).

The display area 35 then displays "CNT," prompting the patient to enter the number of doses in the current prescription. Display area 33 blinks "0" and the patient scans up using the event switch 4 until the desired number is displayed (Step S21). The function button 2a is then pressed to select this number (Step S22).

The display area 35 then prompts the patient to enter the number of days that the current prescription is scheduled to last. Display area 33 blinks "0" and the patient can scan up using the event switch 4 until the desired number is displayed (Step S23). The function button 2a is then pressed to select this number (Step S24).

This completes the setup process. Display area 35 next displays "STRT" and display area 33 displays a question mark ("?"). When the user presses the event switch 4, the device is in an operation mode (Step S25). The operation mode is defined as a mode the device resides in after the user has programmed the desired options. Display 3 may alternately display the current time or the time at which the next dose is to be taken. When the current time is displayed, display area 35 displays "TIME," display area 31 displays the number of the regimen selected by the patient, display areas 33 and 34 display the current time of day, and display area 32 displays the current day of the week. When the time of taking the next dose of medication is displayed, display areas 33 and 34 display the time at which the next dose is to be taken, display area 32 displays the day of the week on which the next dose is to be taken, display area 31 continues to display the number of the selected regimen, and display area 35 displays "NEXT."

After the device is programmed and the event switch 4 is pressed to enter the operation mode, the patient is aware of the day and time at which the first dose of the medication must be taken. At the time for taking the first dose, the microcontroller 9 directs the alarm circuit 8 to emit an audible and/or visible signal to alert the patient that the first dose must be taken at this time (Step S26). The alerting signal continues to be emitted intermittently until the patient takes the dose and presses the event switch 4 or until a prescribed time has elapsed (Step S27). During this time, display area 35 displays "TAKE" indicating that it is time to take the next dose. If the patient takes the dose more than a prescribed time before the scheduled time and presses the event switch 4, the alarm circuit 8 is activated (Step S28) and the display area 35 indicates "ERR" (Step S29) to indicate that the patient has not properly followed the selected regimen.

If the patient fails to take the dose within a prescribed time after the scheduled time while the alarm circuit 8 is activated, display area 35 displays "MISS" (Step S34) indicating that the patient has missed taking the scheduled dose. The display then indicates the time that the missed dose was scheduled to be taken (Step S35) and prompts the patient to direct the device as to how to proceed (Step S36). At this point the patient may press the event switch 4 to maintain the current regimen (Step 37) or may select a new regimen (Step S38).

Upon taking the first dose, the patient presses the event switch 4 which records the taking of the medication and causes the microcontroller to automatically calculate the time/meal at which the next dose of medication must be taken according to the selected regimen and to effect the display of this time on the display 3 (Step S39). The microcontroller also subtracts the dose taken from the total number of doses in the prescription to update the count of remaining doses. This number is displayed in display area 33 while "LEFT" is displayed in display area 35 to indicate the number of doses remaining (Step S40).

Likewise, at the end of each day the microcontroller subtracts one from the total number of days in the prescription to update the count of remaining days. This number is displayed in display area 33 to indicate the number of days remaining (Step S41).

These operating procedures are repeated for as long as the patient's prescription is valid. When the number )f doses in the prescription has been nearly exhausted (i.e., six doses or less remaining), the display indicates "FILL" and the alarm circuit is activated (Step S42). If the patient has the prescription refilled at the direction of a physician, the operating procedures are resumed at Step S21. Otherwise, if the patient has completed his prescription and needs no further medication, the device is turned off by pressing the reset button 2b (Step S43).

Prescription Compliance Device for Multiple Medications

Figure 5:
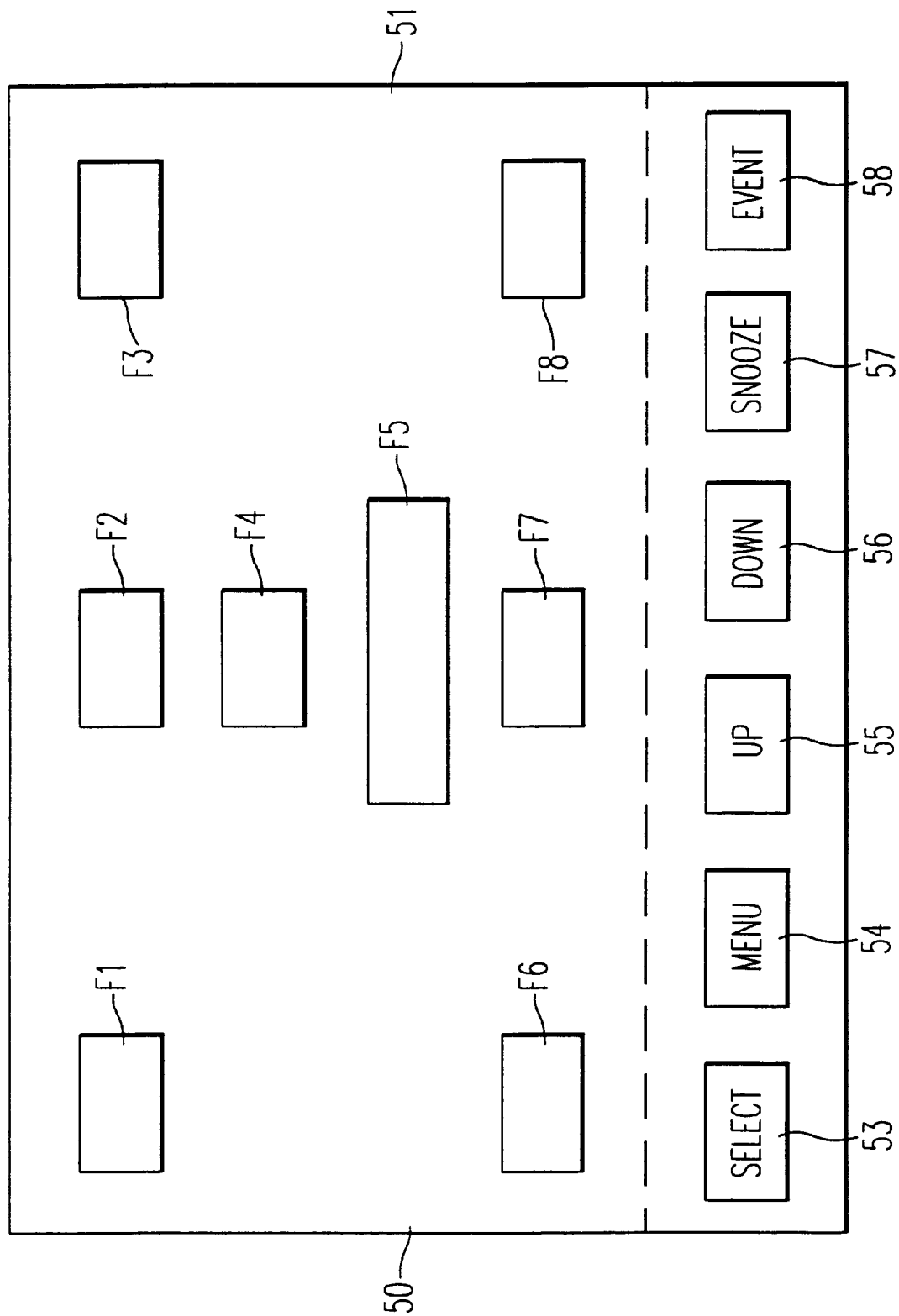
FIG. 5 is an illustration of a prescription compliance device in accordance with a second embodiment of the present invention.

FIG. 5 illustrates a block diagram prescription compliance device according to a second embodiment of the invention. In this embodiment, the user may program the device and monitor the status of multiple medications.

In addition to the central processor and supporting circuitry shown in FIG. 2 for the first embodiment, the device 50 according to the second embodiment includes a display 51 and a key pad 52. The display 51 includes eight character and/or graphical display fields F1–F8 which display information to the user. This information could also be presented using a dot matrix display and/or a scrolling display. Exemplary manners of implementing the display include using a liquid crystal display (LCD), a cathode ray tube (CRT), or a plasma display.

Referring to FIG. 5, the field F1 informs the user if multiple medications are to be taken, F2 informs the user of the specific prescription regimen being used with the medicine identified in F6 and F7, and F3 informs the user as to the status of the alarm or vibrator. When the device 50 is in an "OPERATE" mode, F4 informs the user whether or not to take a medication. If the user is to take a medication, F4 displays the word "TAKE," otherwise F4 displays the word "NEXT." An "OPERATE" mode is defined as a mode in which the device normally resides without an action on the part of the user. During a menu scan operation, the field F4 informs the user of the various options available. The field F4 also provides other information necessary to inform user of the nature or status of information that is being provided in the other fields. The field F5 displays time information, such as the day of the week, hour, minute, and AM or PM, and F6 is an optional character field identifying a memory slot relating to a specific medication F7 displays user programmed information identifying a specific medication and F8 advises the user if a program for a particular medication is operative or if it has been suspended.

As shown in FIG. 5, the device 50 also includes a keypad 52 with six keys: SELECT 53, MENU 54, UP 55, DOWN 56, SNOOZE 57 and EVENT 58. Other keys such as a numeric keypad, an alpha-numeric key pad, or a computer keyboard may be utilized, if desired. These keys are used during programming and operation of the device. The UP 55 and DOWN 56 keys allow the user to scroll through the options under the various menu items and the SELECT 53 key is used to select a desired option. Failure to activate the SELECT 53 key within a prescribed time interval returns the device to the OPERATE mode. Successive activation of the MENU 54 key causes the field F4 to display the menu choices shown in FIG. 6A. Pressing the SELECT 53 key while one of these options is displayed sets the device into the specific operation mode selected. The keypad 52 may be combined with the display 51, as illustrated in FIG. 5, or alternatively the keypad 52 may be separate from the display 51.

The multi-medicine prescription compliance device also includes a SNOOZE switch 57 and an EVENT switch 58. For the medication that is displayed in the fields F6 and F7, pressing the EVENT switch 58 causes the following events to occur. When the field F4 displays the word TAKE, the current date, time, and medication name is recorded, thus signifying the medication was taken. Then the field F4 displays the word NEXT and the next time to take the medication is displayed in the field F5. However, if other medications have earlier take times, the field F4 displays the appropriate NEXT or TAKE screen for that medication. When the field F4 displays the word NEXT and the time to take the medication is within a predetermined time range, the same sequence applies as when the F4 displays the word TAKE. However, when the field F4 displays the word NEXT and the time to take the medication has exceeded the predetermined time range, the current clock time and day are identified with the medication and the event is recorded. If the user fails to take the medication within the predetermined time range, the device advances to the appropriate next take time for that medication. In addition, the SNOOZE button 57 is used to silence the alarm. The alarm will then skip one interval before alerting the user again.

Figure 6A:
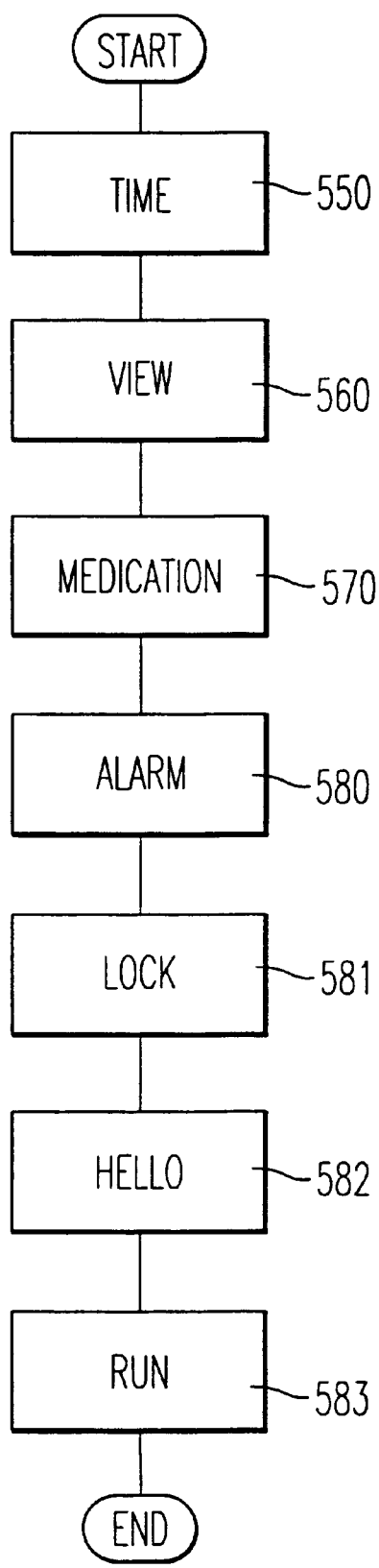
FIG. 6A is a flow diagram illustrating the menu choices available to the user.

The operation of the prescription compliance device according to the second embodiment of this invention will now be described with reference to FIGS. 6A–6H. FIG. 6A illustrates the choices available to the user which can be scrolled through by pressing the MENU 54 key.

The menu choices shown in FIG. 6A include the options of TIME (Step S50), VIEW (Step S60), MEDICATION (Step S70), ALARM (Step S80), LOCK (Step S90), HELLO (Step S100) and RUN (Step S110) which are explained below with respect to FIGS. 6B to 6H. The user scrolls through the options by pressing the MENU 54 key and then selects the desired option with the SELECT 53 key.

Figure 6B:
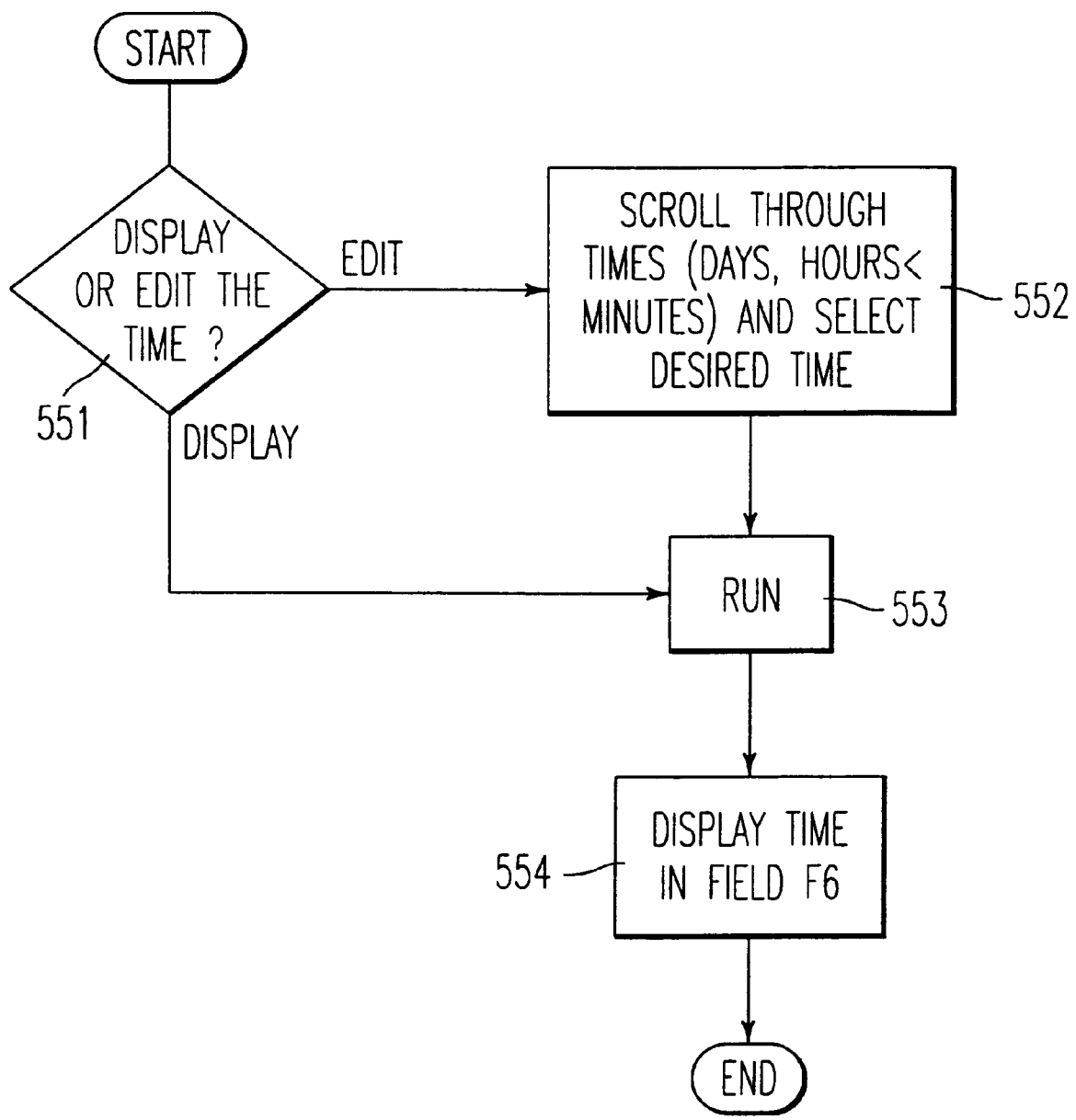
FIGS. 6B–6H are flow diagrams illustrating the steps followed when operating the menu options shown in FIG. 6A.

FIG. 6B illustrates the programming steps required to display or edit the current time. After the TIME option is selected (Step S50) in FIG. 6A, the user has a choice to display the current time or edit the current time (Step S51). If the user chooses to display the current time in Step S51 and executes the RUN option (Step S53), the current time will be displayed in the field F6 (Step S54) and the device returns to the OPERATE mode. If the user chooses to edit the current time in Step S51, the user scrolls through the times (days, hours, minutes) and selects a desired time (Step S52). After executing the RUN option (Step S53), the edited time will be displayed in the field F6 and the device returns to the OPERATE mode.

Figure 6C:
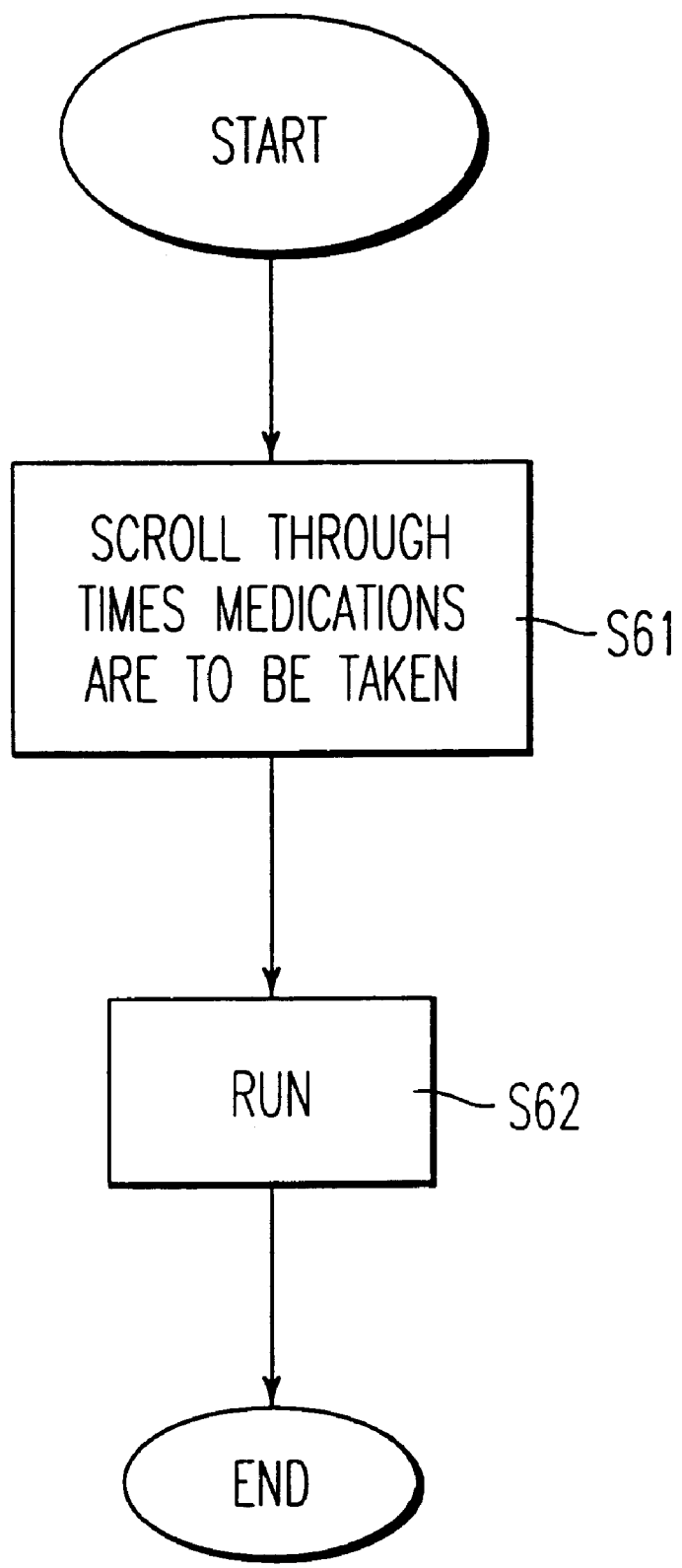

FIG. 6C illustrates the programming steps to view the different medications programmed into the device. After the VIEW option is selected (Step S60) in FIG. 6A, the user scrolls through the times that various medications are to be taken (Step S61). The time the medication is to be taken is displayed in the field F5 and the medicine identifiers are displayed in the fields F6 and F7. The user then selects the RUN option (Step S62) to return the device to the OPERATE mode.

Figure 6D:
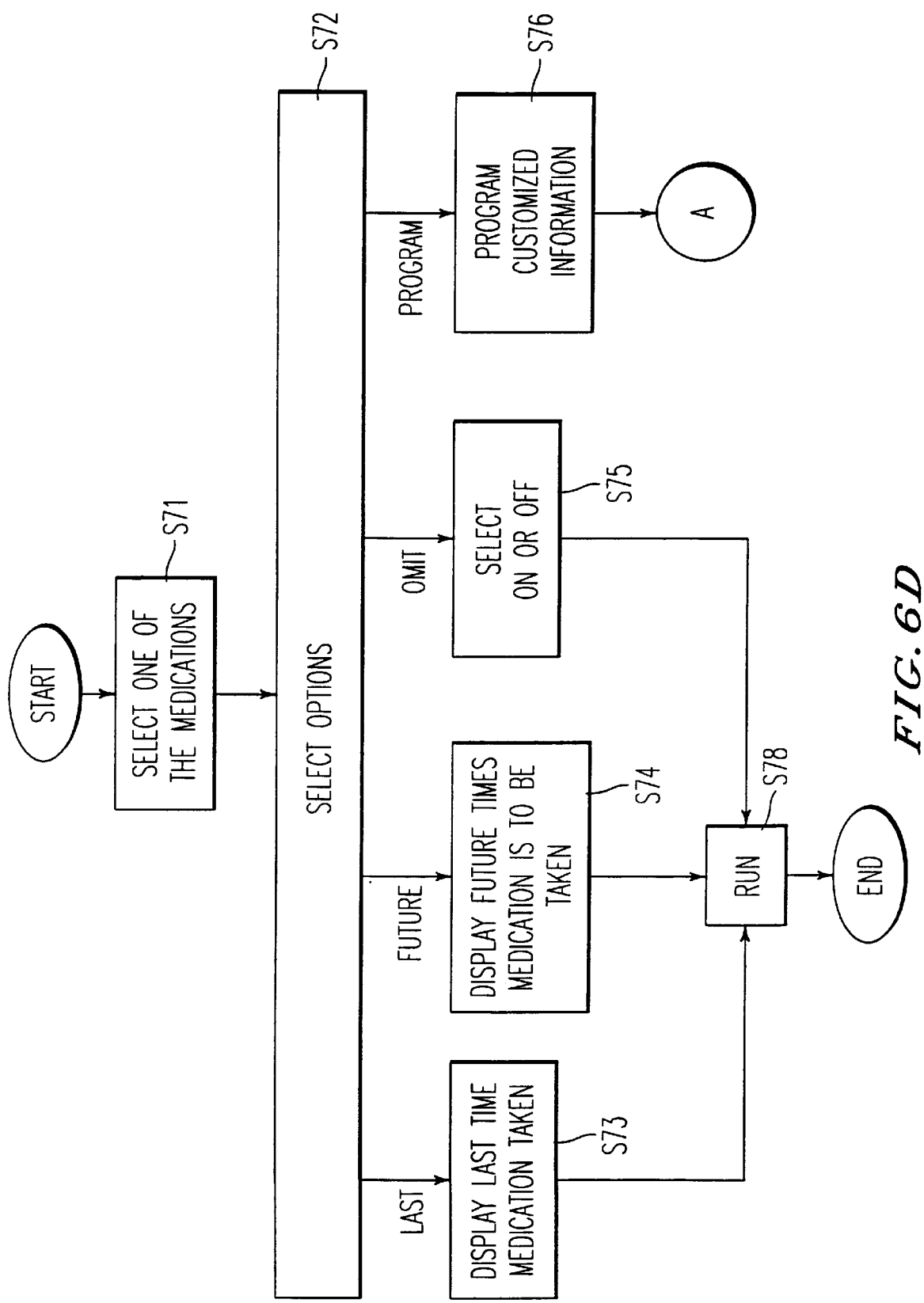
Figure 6E:
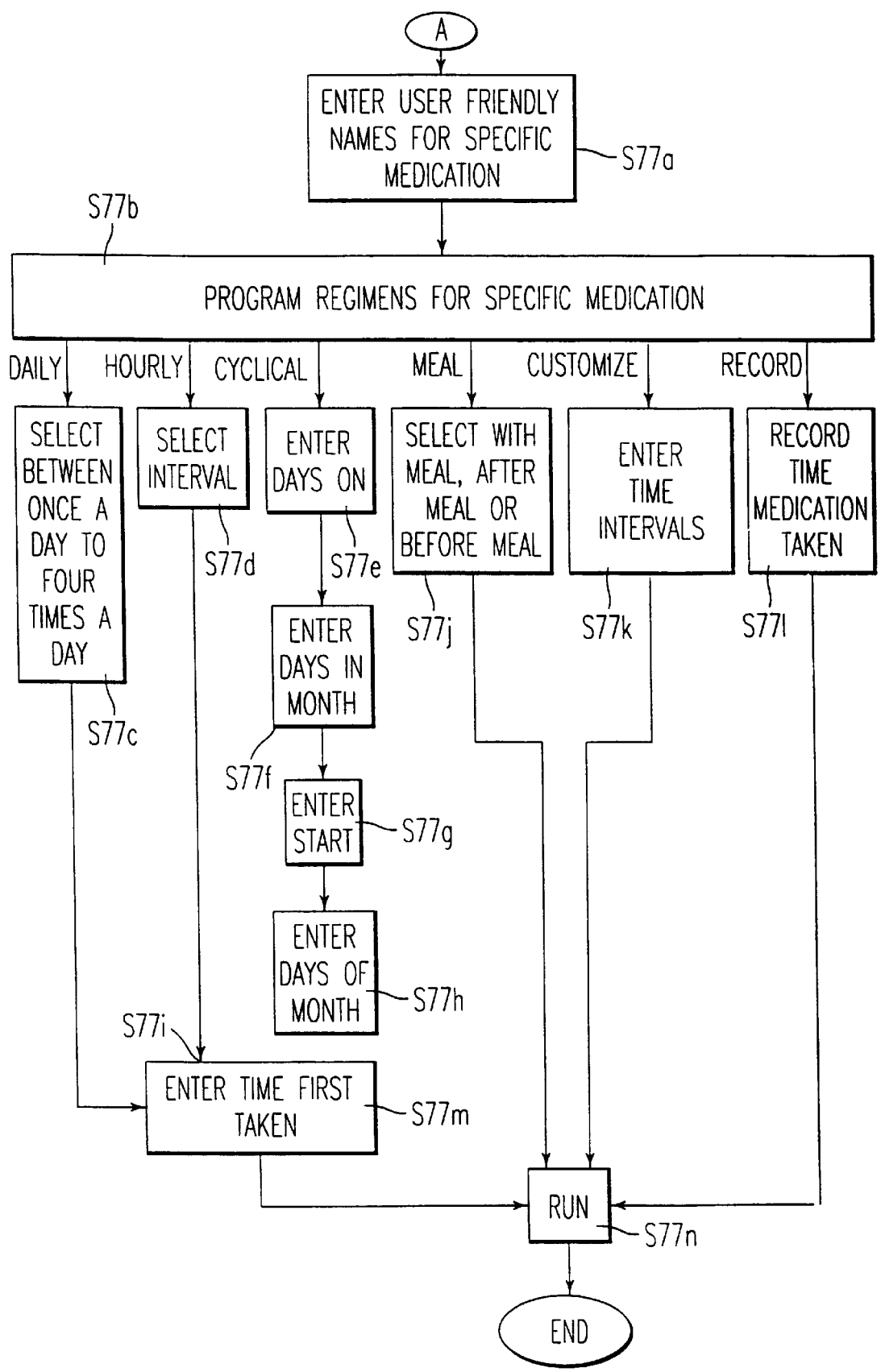

FIG. 6D illustrates the programming steps to view, omit or customize a specific medication. After the MEDICATION option is selected (Step S70) in FIG. 6A, the user scrolls through and selects one of the various medications (Step S71). Upon selecting a medication, the user scrolls through and selects an option (Step S72) including "LAST", "FUTURE", "OMIT" and "PROGRAM". The "LAST" option (Step S73) informs the user the last time the medication was taken. The "FUTURE" option (Step S74) allows the user to scroll through the future times the medication is to be taken and the "OMIT" option (Step S75) allows a user to temporarily turn off the program for the selected medication. The ON/OFF status for the medication is displayed in the field F8. The PROGRAM option (Step S76) allows the user to set (customize) program parameters for the selected medication. FIG. 6E illustrates the programming steps required to set the program parameters.

After the PROGRAM option is selected (Step S76) in FIG. 6D, the user enters customized information identifying the selected medication (Step S77a) in FIG. 6E. The customized information is displayed in the field F7. After Step S77a is performed, the user selects among several regimen options including a daily regimen (i.e., 1/Daily-once per day; 2/Daily-twice a day; 3/Daily-three times a day: and 4/Daily-four times a day) (Step S77c), and an hourly regimen in which the user selects ho irly intervals to take the medication (Step 77d). Also included are a CYCLICAL (monthly cycle), MEAL (meal time), CUSTOMIZE (customized time intervals), and RECORD (record time at which medication was taken) regimens. Upon selecting the CYCLICAL option, the user enters the number of days in the cycle they take the medication (Step S77e). Then, the user enters the days in the month (Step 77f), the start date in the month that the user wants to start taking medication (Step 77g), and the current date of the month (Step S77h). The user also enters the time the first dose is to be taken (Step 77m) for the DAILY, HOURLY, and CYCLICAL regimens. After selecting the MEAL option, the user has a choice to take the medication WITH, AFTER or BEFORE meals (Step S77j). After selecting the CUSTOMIZE option, the user enters a specific time interval (Step S77k). The RECORD option (Step S77l) records the time the medication is taken. The user selects the RUN option (Step S77n) to return the device to the normal operating mode.

Figure 6F:
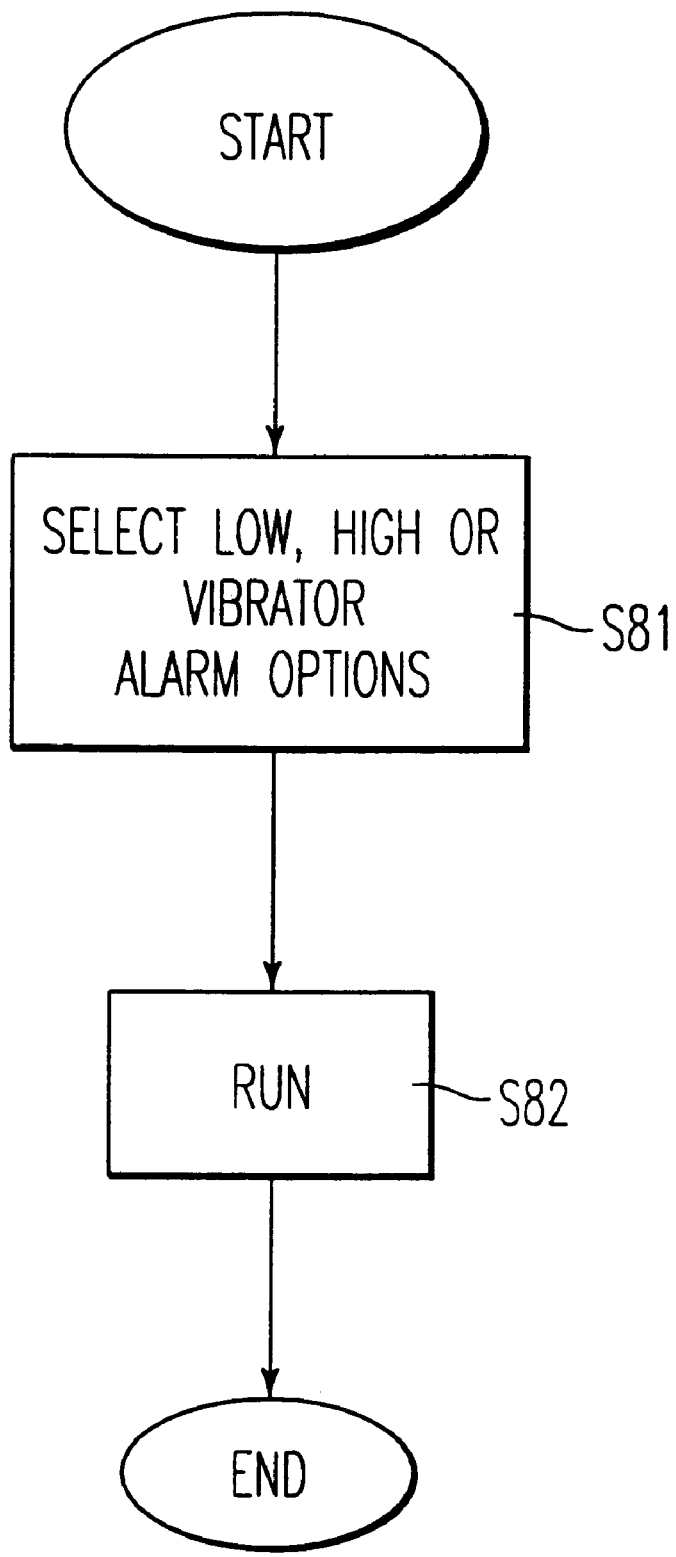

FIG. 6F illustrates the programming steps to program the ALARM options. After the ALARM option (Step S80) is selected in FIG. 6A, the user selects a low, high or vibrator ALARM (Step S81). The user then selects the RUN option (Step S82) to return the device to the normal operating mode.

Figure 6G:
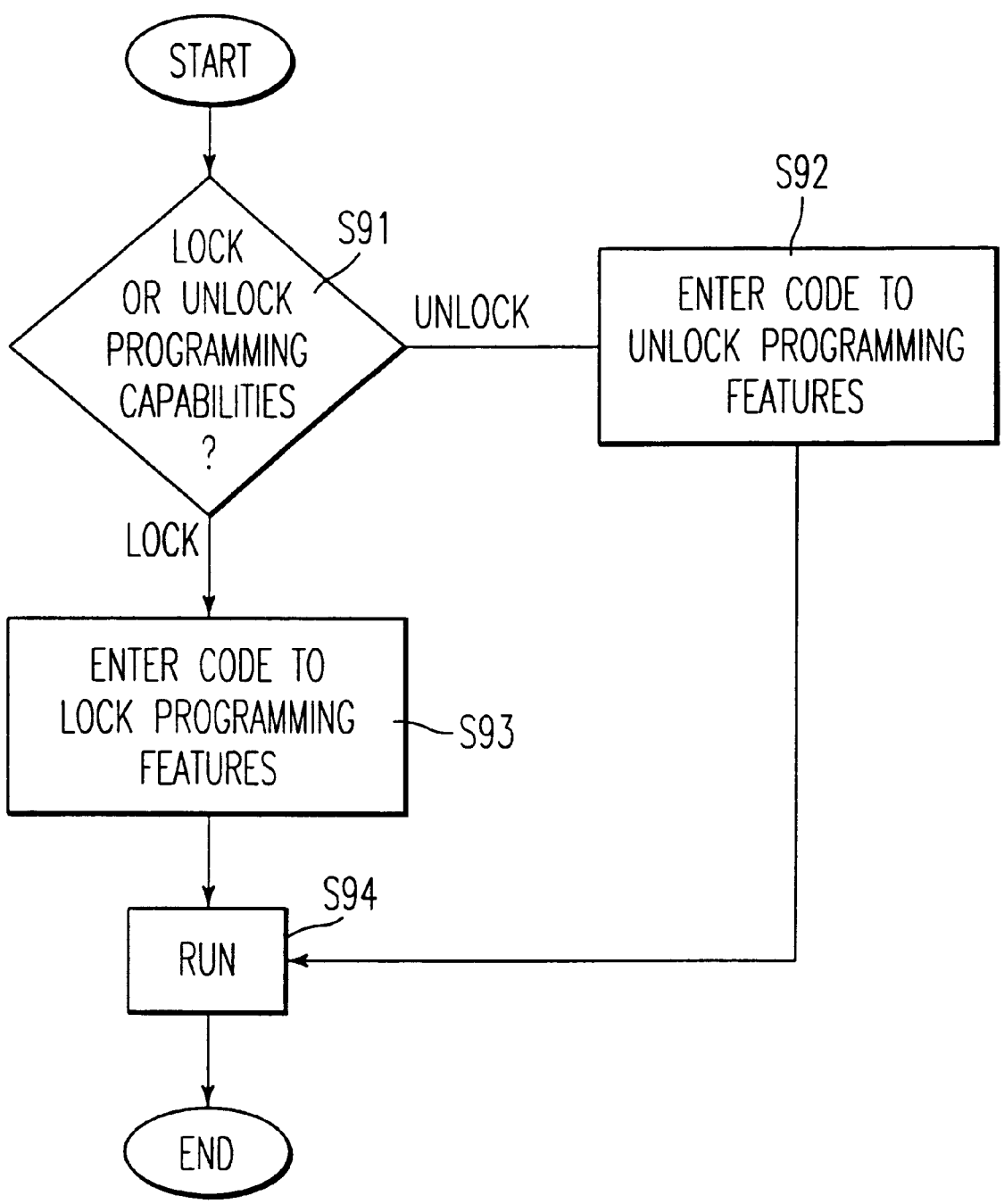

FIG. 6G illustrates the programming steps required to program the LOCK option. After the LOCK option (Step S90) is selected in FIG. 6A, the user has the choice to lock or unlock the programming features of the device (Step S91). If the user wants to lock the programming features, the user enters a code in Step S93. The code may include any combination of numeric or character values. If the user chooses to unlock the programming features, the user enters the code to unlock the device (Step S92). The user then selects the RUN option (Step S94) to return to the device to the OPERATE mode.

Figure 6H:
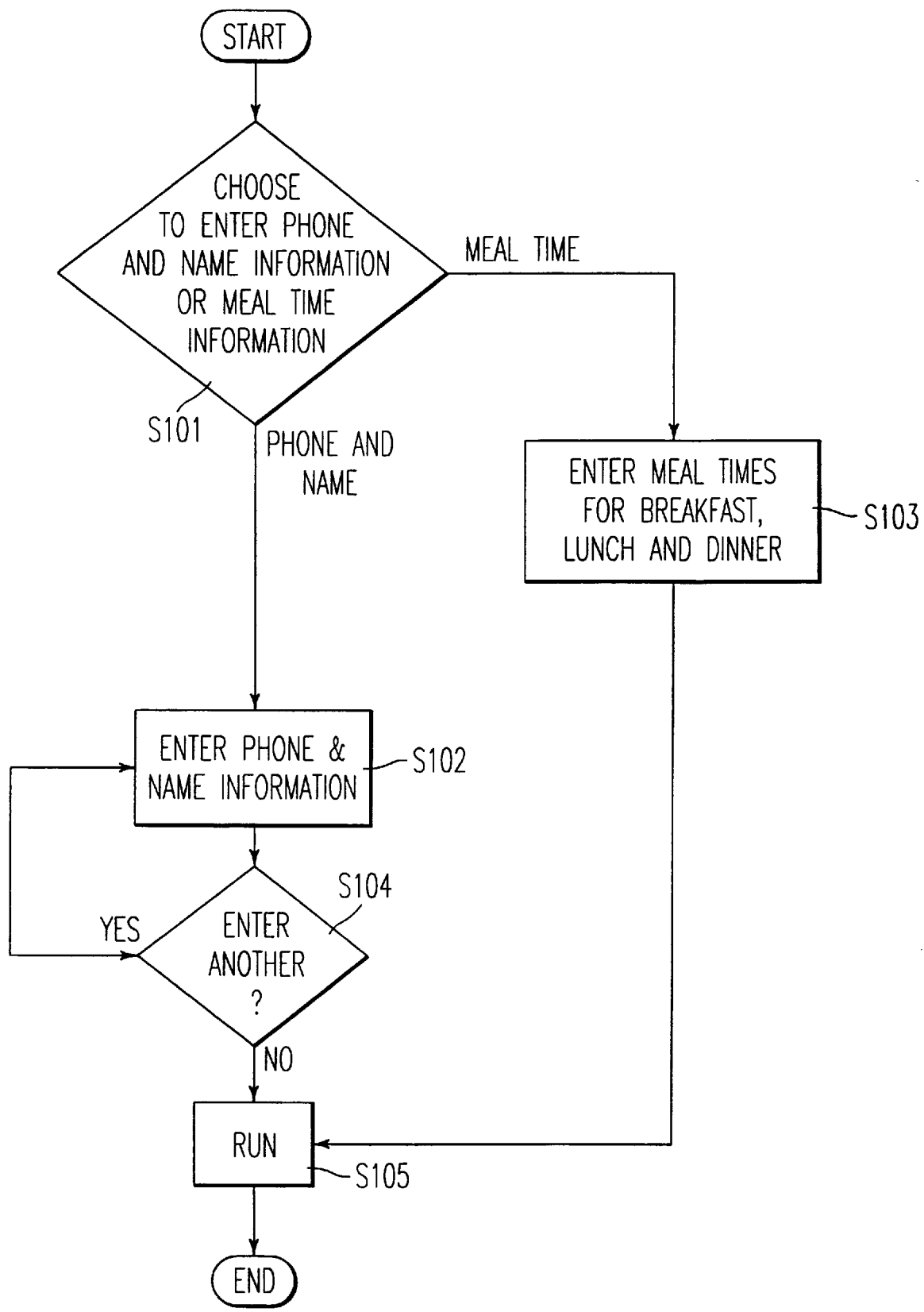

FIG. 6H illustrates the programming steps required to program the HELLO option. After the HELLO option is selected (S100) in FIG. 6A, the user may enter phone and name information or meal time information (Step S101). If the user chooses to enter phone and name information, the user enters the desired phone and name information (Step S102) then has a choice to enter another name and phone number (Step S104). If the user desires to enter another phone and name number (Yes in Step S104), the programming procedure returns to Step S102. If the user does not wish to enter any more phone and name numbers (No in Step S104), the user selects the RUN option (Step S105) and the device returns to the OPERATE mode. If the user chooses to enter meal time information in Step S101, the user enters the desired meal times for breakfast, lunch, and dinner in Step S103. After the desired meal time information is entered, the user selects the RUN option in Step S105 to return the device to the OPERATE mode.

Wireless Output

FIG. 7 illustrates a third embodiment of the present invention. Since the programming and operation of the prescription compliance device according to this embodiment are identical in most aspects to those of the first and second embodiments, a description of the identical features will be omitted. Referring to FIG. 7, the prescription compliance device further includes a wireless transmitter/receiver 40 (Microchip Part No. SFH485) which communicates with an external wireless transmitter/receiver 41 via a wireless link (not shown). The external wireless transmitter/receiver 41 includes a wireless transmitter/receiver 42 and an interface 43 for connection to an input device, such as a personal computer. The interface is preferably a standard RS-232 serial interface, and infrared technology is employed in the preferred embodiment to transmit and receive information. The personal computer runs software by which the device may be programmed via the personal computer instead of directly programming using the function buttons. The above-described programming procedures for the first and second embodiments are carried out in this embodiment on a personal computer. Programming the device is thus made more convenient by simply inputting the above-described parameters (time, meals, number of pills, etc.) via a personal computer keyboard.

The information input by the patient or his medical care provider via a personal computer is transmitted by the wireless transmitter/receiver 42 and received by the wireless transmitter/receiver 40 and processed just as if it were directly input via the buttons described for the first and second embodiments. The wireless transmitter/receiver 40 transmits back to the external device the current status of the device and the information displayed on the display 3,51.

The device of FIG. 7 also includes a non-volatile memory 10 which records the taking of each dose of medication by the patient when the event switch 4,58 is pressed. Information as to which doses have been taken is accessible via the wireless link so that a physician can examine the patient's compliance in taking the medication. The non-volatile memory 10 of the preferred embodiment is an 8 KB serial EEPROM (Microchip Part No. 24LC08B), however equivalent memories may be employed without departing from the scope of this invention. After programming the device on a personal computer, the patient's operation of the device is identical to that described above for the first and second embodiments.

The wireless transmitter/receiver 40 preferably utilizes Amplitude Shift Keying (ASK) modulation to transmit/receive infrared energy to/from the external wireless transmitter/receiver. Infrared technology has been disclosed merely for illustrative purposes and other wireless technologies and modulation methods are contemplated to be within the scope of the invention.

In addition, each prescription compliance device has a unique identification number assigned thereto and stored in its program memory 20 for the purpose of identifying a particular device when programming from a remote location.

With regard to programming the device, parameters such as the day, time of day, and other parameters may be set in a global register, whereas medication specific parameters are programmed within a unique register. An additional capacity may be included to allow the user to review the information programmed into the device for each of the registers and to review any other pertinent information. This information may be reviewed at the level of the device itself and/or through the wireless computer interface.

The activation of the event switch 4,58 will cause temporal data to be stored in a non-volatile memory. In addition, such temporal data will have associated with it an identifying character so that a utilization of a specific medication or therapy can be tracked.

In addition to or as an alternative to identifying the individual registers by characters or symbols, the device may also provide user-friendly information, such as information identifying the specific medication associated with a register by name or description (i.e. yellow pill, water pill, etc.). Additionally, instructions may be provided in conjunction with an alarm providing the user with useful information (i.e. take with food; avoid milk, etc.). Both types of such additional information would be accessible to each register to recall and display at appropriate times in either voice or character formats as discussed below.

The wireless emissions of the device can also be used as transducing the elements to activate secondary apparatuses. Thus, the emission of a wireless signal in conjunction with an alarm can be used as a signal to activate secondary alarms. The secondary alarms can be used to alert individuals who are hearing or vision impaired, to alert delivery systems to dispense medication to individuals who are mentally or physically handicapped, or to activate any of a variety of other types of apparatuses.

Within institutional settings, emissions from the prescription compliance device which are triggered by the alarm logic, may be used in conjunction with medication or therapy dispensing stations, or similarly, to alert staff that the time has arrived to provide a specific medication or therapy to a patient. Thus, according to the present invention, scheduling and planning of therapy regimens in the pharmacy, by the physician, or by any other care provider, may be programmed into the prescription compliance device. In this embodiment, the device can perform a function of instructing staff to provide medication or therapy in a prescribed manner and/or at prescribed times.

In the present invention, this prescription compliance device is equipped with a capacity for wireless emissions that are output in conjunction with activation of the event switch or passively by opening the medicine bottle, etc. The wireless emissions carry the unique unit specific signature and can be collected by independent receivers. Therefore, collection of emission data can be used to evaluate and monitor the appropriate dispensing of medication and therapy, and to provide an alert/alarm condition if serious omission or error occurs (e.g., a medication was not dispensed properly).

Wireless emission output may also be used to effect concurrent signal emission by another apparatus or device. Concurrent wireless emission by the prescription compliance device and other apparatuses could be received by an independent recorder in very close time sequences, thus allowing temporal and proximity relation of action and instruments to be established. For example, the activation of the "Event Switch" on a prescription compliance device would emit a signal that would be collected by the independent receiver and would also cause an appropriate patient identifying device to emit a signal. This signal would also be collected by the receiver. Through correlation of the receiver identity, prescription compliance device identity, and patient identity, a data set can be generated establishing a relationship between a specific action, a specific place, a specific medication, and a particular patient.

Attachments

Figure 8A:
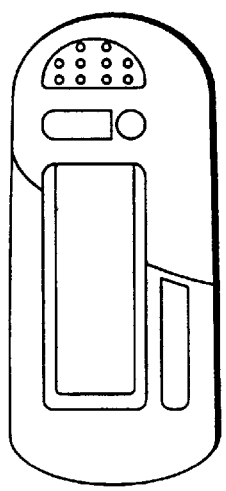
FIG. 8A illustrates the prescription compliance device according to the present invention as a free standing device.
Figure 8C:
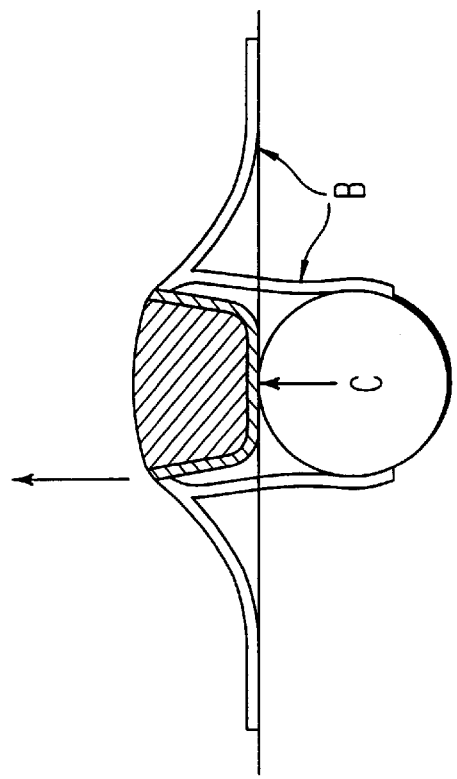
FIG. 8C illustrates a cross-sectional view of the prescription compliance device attached to a bottle according to the present invention.
Figure 8B:
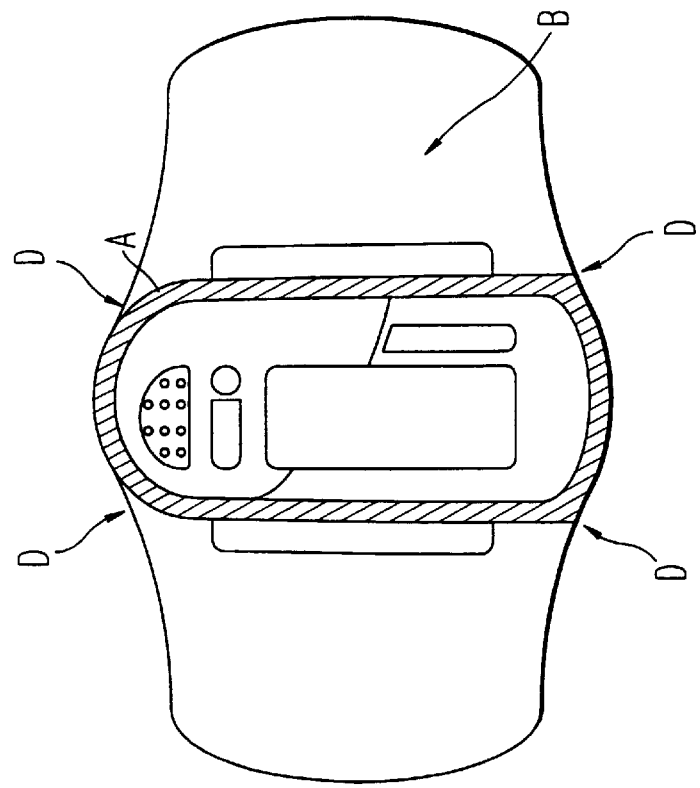
FIG. 8B illustrates a top view of the prescription compliance device and attachment mechanism according to the present invention.

FIGS. 8A, 8B and 8C illustrate the prescription compliance device attached to a variety of containers and surfaces that are either flat or curved. FIG. 8A shows the prescription compliance device as a free standing device which is housed in a plastic casing that has an accommodation on the back surface to permit attachment to a chain or loop that facilitates use as a key chain or pendent (not shown). The device fits into a collar (A in FIGS. 8B and 8C) that are flexible and can bend to accommodate the shape of curved containers or flat surfaces. The "wings" and back surface of the collar are coated with adhesive which attaches the attachment appliance to the surface or container (FIG. 8C). In applications where a narrow construct is required, the "wings" may be clipped off at points D (in FIG. 8B) and attachment to the surface can be achieved solely through the adhesive on the back of the collar C (in FIG. 8C)

Thus, the prescription compliance device according to this invention may be attached to medication containers by adhesives, straps, velcro, mechanical attachment, integration as a component of the container itself, or by any other manner of attachment. The device also operates freestanding, and need not be attached to a medication container.

The device can be utilized in conjunction with or as a part of a wide array of medicine delivery systems and free standing, units. Free standing units independent of the medical container include use as, or as a part of a clock, pendent, key chain or watch. Other free standing applications include configurations similar to those used for beepers or cellular telephones or any other similar configuration that can easily be carried by a person. In addition to attaching the device to the medicine container or integration as a part of the medicine container, the current invention describes prescription compliance devices that can be used with or are a part of blister packaging, medicine cabinets, pill box or any other container intended for distributing medication. Additionally, the device can be integrated with, or used in conjunction with a cabinet, cart or other similar apparatus that is used in conjunction with dispensing medicine or therapy in an institutional setting.

Alarms

As discussed above, the device triggers circuits to alert the patient when to take a dose of medication. These alarm capabilities include, in addition to audio and visual signals, tactile signaling, such as a vibrator or comparable mode of signaling, voice signaling achieved through a recording or digital generation, and the use of a wireless output as a transducing element to activate a triggering of secondary devices (e.g., alarms, patient assistance equipment, etc.) or to alert medical personnel or other personnel that some form of action should be taken (e.g., providing medication or therapy). The avenue via which the prescription compliance device communicates information to the user includes tactile and visual and auditory signaling.

The use of tactile stimulation, such as the vibrator used in a pager, or some similar stimulus will provide the user with a discrete signal that can alert the user without alerting others in his/her company. Operation of a tactile stimulation will occur in a manner analogous to that described for the visual and auditory stimuli.

The device according to the present invention also includes the use of recorded signaling to provide the user with identification and/or instructional information. In order for prescription devices to achieve these capabilities, they may be equipped with a microphone, speaker and solid state recording device. In the recording mode, the user can provide vocal input regarding identification of medication and/or proper usage. Utilization of user (or medical care provider) recorded information will occur per logic employed at the level of the device's microprocessor(s) and may incorporate prerecorded information in addition to that recorded by the user. Thus, with the multi-medicine device described, the logic in a specific register may be used to dictate playback of a recorded sequence such as "10 PM; Take Yellow Pills; Take with food." Such a sequence may combine user recorded and prerecorded signaling to alert the user to therapy identification, the time of utilization, special instructions, and any other parameters that might be appropriate. Such sequences are appropriately utilized within specific registers in multi-medication devices, thus providing the user with the proper timing and practical advice for the correct use of specific medications.

In addition, a user initiated action may be required to initiate the display of either visual or recorded identification and instructional information. Thus, the prescription device may first emit an audio, visual or tactile stimulus, and then an action by the user will cause the device to display the appropriate audio and/or visual information. Display of such audio or visual information may be accomplished in a manner so as to preserve the privacy of the user in hearing or viewing such information (e.g., an ear phone).

Dosing Schedules

TABLE 1 summarizes dosing time intervals for morning, midday, afternoon, etc. Normally a patient is awake for 14 hours and it is over this interval that a patient is most likely to take medication prescribed in a given day. The 14 day is divided into a series of time intervals desirable for the patient to take medication. Alternatively, the dosing time intervals may correspond to meal times (e.g., with, before, and after breakfast, lunch, etc.).

TABLE 1

| DOSAGE TIME | INCREMENT | TIME (example) |
|---|---|---|
| 1st (Morning) | 0 hr | 8 AM (first dose of day) |
| 2nd (Mid day) | 4 hr | 12 PM |
| 3rd (Afternoon) | 7 hr | 3 PM |
| 4th (Evening) | 9 hr | 5 PM |
| 5th (Late evening) | 12 hr | 10 PM |
| 6th (Bedtime) | 14 hr | 10 pm |

FIG. 9 illustrates additional programming regimens which allow the user to easily adjust a medication-taking regimen.

Utilization of the specific times generated in such a matrix as shown in Table 1 allows simple definition of appropriate times for the patient to take medication under the most common regimens identified in FIG. 9 as Regimens 1, 2, 3 and 4. Medications not prescribed by these straight forward regimens may be handled by additional regimens. Regimen 0 is a fully custom regimen which allows the patient to define up to, for example, 9 specific times in a day when medication is to be taken. Regimen 5 is designed for medications that must be taken at prescribed intervals and may accommodate intervals of up to 99 hours. Regimen 6 operates to define a specific interval after taking a dose of medication prior to which another dose should not be taken. Regimen 7 defines a monthly cycle for taking medication (i.e., the patient is advised when to and when not to take medication over the course of a month or other cycle). Regimen 8, 9, and 10 are for use with medications that are to be taken in conjunction with meals. These regimen may have default times of 8:00 AM, 12:30 PM, and 6:00 PM, but the patient is able to set times appropriate for his own schedule. Regimen 11 is a record only mode where only activation of the event button is recorded.

Programming the regimens shown in FIG. 9 is similar to the programming steps described in the first and second embodiments. Briefly, to program one of the regimens in FIG. 9, the user sets the current time of the day and selects a desired regimen number. To program regimen 0, the times for T1–T9 are set. The chain of times may be terminated by setting 0:00. For Regimens 1–4, the time for the first dose to be taken is set and the take times are automatically calculated as appropriate.

For Regimen 5, the time for the first dose to be taken and the desired time interval is set. The time interval may be set as any number between 0 and 100 or it may be selected from the sequence 1,2,3,4,6,8,12,24,36,48,60,72,84,96 hr. The take times are automatically calculated by adding the interval time to the first dose time or the previously calculated take time.

For Regimen 6, the time interval is set as any number between 0 and 100 or it may be selected from the sequence 1,2,3,4,6,8,12,24,36,48,60,72,84,96 hrs. The take times are automatically calculated by adding the interval time to the time the first time or the previously calculated take time.

For Regimen 7, the time for the first dose to be taken is set. Then the days on (i.e., the number of consecutive days in which the prescription should be taken) is set. The days in the cycle (i.e., days in month or number of days), and the current date or number of days in the cycle is set. The starting date in the cycle is set and the take times are automatically calculated. The device additionally advises the user on what days in the cycle medication should be taken. When the user enters the first take time in a new cycle, the device will prompt the user to enter a new value for the day in the cycle. For example, assume the user wanted to take medication from the 16th to the 25th of each month and today is April 9th. In this case, Day ON=10, Days in Cycle=30, Current Date=9, and Starting Date=16.

For Regimen 8, the user scans and selects a default time for Breakfast (08:00 AM), Lunch (12:30 PM), and Dinner (6:00 PM) and additionally the user has the ability to alter the default time.

For Regimen 9, the user scans and selects a default time for Breakfast (08:00 AM), Lunch (12:30 PM), and Dinner (6:00 PM) (and may alter the default time) and the take times are automatically calculated by adding 2 hours to the selected meal times.

For Regimen 10, the user scans default times for Breakfast (08:00 AM), Lunch (12:30 PM), and Dinner (6:00 PM) (and may alter the default time) and the take times are automatically calculated by subtracting 1 hour from the selected meal times.

The event switch shown in the first and second embodiments should be of a size such that activation by an elderly person would not be difficult while at the same time safeguarding against accidental activation. The reset button is of a size such that activation thereof requires a thin, needle-shaped object so as to safeguard against the accidental turning off of the device. Accidental depression of the function button is harmless since this button has no effect when the device is not in the setup mode except to de-activate the alarm circuit.

Provision is also made for a low battery indication. After the passage of a certain number of days from when the battery was last replaced, the display displays "BAT" to indicate that the battery should soon be replaced.

Electronic configuration and programming parameters

This invention may be conveniently implemented using a conventional general purpose digital computer or microprocessor programmed according to the teachings of the present specification, as will be apparent to those skilled in the computer art. Appropriate software coding can readily be prepared by skilled programmers based on the teachings of the present disclosure, as will be apparent to those skilled in the software art. The invention may also be implemented by the preparation of application specific integrated circuits or by interconnecting an appropriate network of conventional component circuits, as will be readily apparent to those skilled in the art.

The present invention includes a computer program product which is a storage medium including instructions which can be used to program a computer to perform a process of the invention. The storage medium can include, but is not limited to, any type of disk including floppy disks, optical discs, CD-ROMs, and magneto-optical disks, ROMs, RAMs, EPROMs, EEPROMs, magnetic or optical cards, or any type of media suitable for storing electronic instructions.

Obviously, numerous modifications and variations of the present invention are possible in light of the above teachings. The specific parameters mentioned in conjunction with the description of the invention have been set forth solely for illustrative purposes and are not limiting of the scope of the invention in any way. It is therefore to be understood that within the scope of appended claims, the invention may be practiced otherwise than as specifically described herein.

What is claimed as new and is desired to be secured by Letters Patent of the United States is:

1. A computer program product for operating a prescription compliance device, comprising:
    (a) a first computer code configured to switch the device to a setup state;
    (b) a second computer code configured to program the current time into the device;
    (c) a third computer code configured to select one of a plurality of pre-programmed commonly prescribed prescription-taking regimens;
    (d) a fourth computer code configured to program a time of day a first use of prescription is to be taken in accordance with the selected regimen;
    (e) a fifth computer code configured to switch the device from a setup state to an operation state; and
    (f) a sixth computer code configured to indicate to the device that a prescription has been followed;
    wherein at least one of the plurality of pre-programmed prescription-taking regimens causes calculation of acceptable times during which the patient is scheduled to use the prescription, and
    wherein the calculated times are based on the following factors:
        1) a preferred time of day at which the patient is to take a first use of the prescription;
        2) a regimen specific predetermined interval of time between uses of the prescription; and
        3) a regimen specific predetermined time range during which it is medically acceptable for the patient to use the prescription.

2. The computer program product according to claim 1, wherein any of said plurality of pre-programmed prescription-taking regimens corresponds to be used with any of a plurality of prescriptions.

3. The computer program product according to claim 2, further comprising:
    (g) a seventh computer code configured to map an acronym input by the user and which corresponds to one of the plurality of prescriptions so as to allow the user to input acronyms to define specific prescriptions.

4. The computer program product according to claim 2, wherein at least one of said plurality of pre-programmed prescription-taking regimens calculates times when said patient is scheduled to use at least one of said plurality of prescriptions based on predetermined time intervals and a time a first use of said prescription is to be used.

5. The computer program product according to claim 1, further comprising:
    (g) a seventh computer code configured to program a day on which the first dose of medication is to be taken.

6. The computer program product according to claim 1, further comprising:
    (g) a seventh computer code configured to program a number of doses or number of days until prescription renewal;
    (h) an eigth computer code configured to alert the user of the prescription renewal; and
    (i) a ninth computer code configured to allow the number of doses or number of days to be reset.

7. The computer program product according to claim 1, wherein the computer code (a) is executed by activating a reset button.

8. The computer program product according to claim 1, wherein the computer code (b) is executed by activating an event switch to scan through times as displayed on a display and activating a function button to select the current time when displayed.

9. The computer program product according to claim 1, wherein the computer code (c) is executed by activating an event switch to scan through the pre-programmed regimens as displayed on a display, and activating a function button to select an appropriate regimen when displayed.

10. The computer program product according to claim 1, wherein the computer code (d) is executed by activating an event switch to scan through times or events as displayed on a display, and activating a function button to select an appropriate time or event when displayed, or activating an event switch to designate pre-programmed default times in accordance with a selected regimen.

11. The computer program product according to claim 5, wherein the computer code (g) is executed by activating an event switch to scan through days as displayed on a display, and activating a function button to select an appropriate day when displayed.

12. The computer program product according to claim 6, wherein the computer code (g) is executed by activating an event switch to scan through numbers as displayed on a display, and activating a function button to select an appropriate number when displayed.

13. The computer program product according to claim 1, wherein the computer code (e) is executed by activating an event switch after one of the regimens has been selected and the device has been programmed.

14. The computer program product according to claim 1, wherein the computer code (f) is executed by activating an event switch after a dose of medication has been taken so as to cause the device to display a time at which a next dose of the medication is to be taken.

15. The computer program product according to claim 2, wherein the computer codes (a)–(f) are executed by activating an input device which communicates with the prescription compliance device.

16. The computer program product according to claim 15, wherein the input device communicates with the prescription compliance device via a wireless link and comprises a personal computer.

17. The computer program product according to claim 16, wherein the wireless link is an infrared link.

18. The computer program product according to claim 2, further comprising:
  (g) a seventh computer code configured to record times at which doses of medication are taken when an event switch is activated.

19. The computer program product according to claim 18, further comprising:
  (h) an eighth computer code configured to access the recorded times via the wireless link.

20. A computer program product for operating a prescription compliance system, comprising:
  a first computer code configured to transmit, from a prescription compliance device, a signal directly or indirectly to a patient identifying device and a recorder when a prescription is to be administered or has been administered;
  a second computer code configured to transmit a patient identification signal to the recorder when the patient has taken the prescription;
  a third computer code configured to record the signals transmitted by the prescription compliance device and the patient identifying device; and
  a fourth computer code configured to confirm that the prescription was taken by the identified patient by correlating the recorded signals.

21. The computer program product according to claim 20, further comprising:
  a fifth computer code configured to identify a location of the recorder; and
  a sixth computer code configured to correlate the prescription-taking event with the patient and the location.

22. The computer program product according to claim 1, further comprising:
  a seventh computer code configured to notify the user that the prescription can be used in a medically acceptable time range.

23. A prescription compliance device comprising:
  a microcontroller;
  a program memory storing data representing a plurality of pre-programmed commonly prescribed prescription-taking regimens;
  a selector selecting one of the regimens and programming the device in accordance therewith, the selector including an event switch which is activated in conjunction with a patient taking a prescription corresponding to a respective prescription-taking regimen to register use of the prescription;
  a display; and
  a skip mechanism configured to allow the patient to skip using the prescription,
  wherein the event switch causing the microcontroller to effect the display of the time at which a next use of the prescription is scheduled, in accordance with the regimen selected by the selector,
  wherein at least one of the plurality of pre-programmed prescription-taking regimens causes calculation of acceptable times during which the patient is scheduled to use the prescription, and
  wherein the calculated times are based on the following factors:
    1) a preferred time of day at which the patient is to first use the prescription;
    2) a regimen specific predetermined interval of time between uses of the prescription; and
    3) a regimen specific predetermined time range during which it is medically acceptable for the patient to use the prescription.

24. The device according to claim 23, wherein the skip mechanism comprises a snooze button which silences an alarm activated when the patient misses a dose of medication.

25. A prescription compliance device comprising:
  control means for controlling an operation of the prescription compliance device;
  program memory means for storing data representing a plurality of pre-programmed commonly prescribed prescription-taking regimens;
  select means for selecting one of the regimens and programming the device in accordance therewith, the select means including an event switch which is activated in conjunction with a patient using the prescription corresponding to a respective prescription-taking regimen to register use of the prescription;
  skipping means for allowing the patient to skip one use of the prescription; and
  display means for displaying prescription information to the patient,
  wherein the event switch causing the control means to effect the display means of the time at which a next use of the prescription is scheduled, in accordance with the regimen selected by the select means,
  wherein at least one of the plurality of pre-programmed prescription-taking regimens causes calculation of acceptable times during which the patient is scheduled to use the prescription, and
  wherein the calculated times are based on the following factors:
    1) a preferred time of day at which the patient is to first use the prescription;
    2) a regimen specific predetermined interval of time between uses of the prescription; and
    3) a regimen specific predetermined time range during which it is medically acceptable for the patient to use the prescription.

26. The device according to claim 25, wherein the skipping means comprises a snooze button which silences an alarm activated when the patient misses use of the prescription.

27. A prescription compliance method, comprising the steps of:

controlling an operation of the prescription compliance device;

storing data representing a plurality of pre-programmed commonly prescribed prescription using regimens;

selecting one of the regimens and programming the device in accordance therewith;

activating an event switch in conjunction with a patient making use of the prescription corresponding to a respective prescription-taking regimen to register use of the prescription;

allowing the patient to skip a use of the prescription; and displaying prescription information to the patient, wherein the event switch causes the control step to effect the display step of the time at which a next use of prescription is scheduled to be taken, in accordance with the regimen selected by the selecting step, wherein at least one of the plurality of pre-programmed prescription utilization regimens causes calculation of acceptable times during which the patient is scheduled to use the prescription, and wherein the calculated times are based on the following factors:
1) a preferred time of day at which the patient is to make first use of the prescription;
2) a regimen specific predetermined interval of time between uses of the prescription; and
3) a regimen specific predetermined time range during which it is medically acceptable for the patient to use the prescription.

28. The method according to claim 27, wherein the skipping step comprises a snooze button which silences an alarm activated when the patient misses a use of the prescription.

29. A prescription compliance device comprising:

a microcontroller;

a program memory storing data representing a plurality of pre-programmed commonly prescribed prescription using regimens;

a selector selecting one of the regimens and programming the device in accordance therewith, the selector including an event switch which is activated in conjunction with use of the prescription by the patient corresponding to a respective prescription-utilization regimen to register use of the prescription; and a display, wherein the event switch causing the microcontroller to effect the display of the time at which a use of the prescription is scheduled, in accordance with the regimen selected by the selector, and wherein at least one of the pre-programmed commonly prescribed prescription-utilization regimens corresponds to a prescription to be used on a cyclical basis, wherein at least one of the plurality of pre-programmed prescription-utilization regimens causes calculation of acceptable times during which the patient is scheduled to make use of the prescription, and wherein the calculated times are based on the following factors:

1) a preferred time of day at which the patient is to make first use of the prescription;
2) a regimen specific predetermined interval of time between uses of the prescription; and
3) a regimen specific predetermined time range during which it is medically acceptable for the patient to use the prescription.

30. A prescription compliance device comprising:

control means for controlling an operation of the prescription compliance device;

program memory means for storing data representing a plurality of pre-programmed commonly prescribed prescription-utilization regimens;

select means for selecting one of the regimens and programming the device in accordance therewith, the select means including an event switch which is activated in conjunction with a patient making use of a prescription corresponding to a respective prescription-utilization regimen to register the use of the prescription; and display means for displaying prescription information to the patient, wherein the event switch causing the control means to effect the display means of the time at which a next use of the prescription is scheduled, in accordance with the regimen selected by the select means, and wherein at least one of the pre-programmed commonly prescribed prescription-utilization regimens corresponds to a medication to be taken on a cyclical basis, wherein at least one of the plurality of pre-programmed prescription-utilization regimens causes calculation of acceptable times during which the patient is scheduled to use the prescription, and wherein the calculated times are based on the following factors:
1) a preferred time of day at which the patient is to first use the prescription;
2) a regimen specific predetermined interval of time between uses of the prescription; and
3) a regimen specific predetermined time range during which it is medically acceptable for the patient to make use of the prescription.

31. A prescription compliance method, comprising the steps of:

controlling an operation of the prescription compliance device;

storing data representing a plurality of pre-programmed commonly prescribed medication-taking regimens;

selecting one of the regimens and programming the device in accordance therewith;

activating an event switch in conjunction with a patient making use of a prescription corresponding to a respective prescription-utilization regimen to register the use of the prescription; and displaying prescription information to the patient, wherein the event switch causes the control step to effect the display step of the time at which a next use of the prescription is scheduled, in accordance with the regimen selected by the selecting step, and wherein at least one of the pre-programmed commonly prescribed prescription-utilization regimens corresponds to a prescription to be used on a cyclical basis, wherein at least one of the plurality of pre-programmed prescription-utilization regimens causes calculation of acceptable times during which the patient is scheduled to make use of the prescription, and wherein the calculated times are based on the following factors:
1) a preferred time of day at which the patient is to make first use of the prescription;
2) a regimen specific predetermined interval of time between uses of the prescription; and
3) a regimen specific predetermined time range during which it is medically acceptable for the patient to use the prescription.

32. A prescription compliance device comprising:

a microcontroller;

a program memory storing data representing a plurality of pre-programmed commonly prescribed prescription-utilization regimens;

a selector selecting one of the regimens and programming the device in accordance therewith, the selector including an event switch which is activated in conjunction with a patient making use of the prescription corresponding to a respective prescription-utilization regimen to register use of the prescription; and a display, wherein the event switch causing the microcontroller to effect the display of the time at which a next use of the prescription is scheduled, in accordance with the regimen selected by the selector, and wherein at least one of the pre-programmed commonly prescribed prescription-utilization regimens corresponds to a prescription to be followed on hourly intervals up to 99 hours.

33. The device according to claim 32, wherein at least one of the plurality of pre-programmed prescription-utilization regimens causes calculation of acceptable times during which the patient is scheduled to make use of the prescription, and wherein the calculated times are based on the following factors:
1) a preferred time of day at which the patient is to make first use of the prescription;
2) a regimen specific predetermined interval of time between uses of the prescription; and
3) a regimen specific predetermined time range during which it is medically acceptable for the patient to use the prescription.

34. A prescription compliance device comprising:

control means for controlling an operation of the prescription compliance device;

program memory means for storing data representing a plurality of pre-programmed commonly prescribed prescription-utilization regimens;

select means for selecting one of the regimens and programming the device in accordance therewith, the select means including an event switch which is activated in conjunction with a patient making use of a prescription corresponding to a respective medication-taking regimen to register the use of the prescription; and display means for displaying prescription information to the patient, wherein the event switch causing the control means to effect the display means of the time at which a next use of the prescription is scheduled, in accordance with the regimen selected by the select means, and wherein at least one of the pre-programmed commonly prescribed prescription-utilization regimens corresponds to a prescription to be used on hourly intervals up to 99 hours.

35. The device according to claim 34, wherein at least one of the plurality of pre-programmed prescription-utilization regimens causes calculation of acceptable times during which the patient is scheduled to make use of the prescription, and wherein the calculated times are based on the following factors:
1) a preferred time at which the patient is to first use the prescription;
2) a regimen specific predetermined interval of time following the prescription; and
3) a regimen specific predetermined time range during which it is medically acceptable for the patient to make use of the prescription.

36. A prescription compliance method, comprising the steps of:

controlling an operation of the prescription compliance device;

storing data representing a plurality of pre-programmed commonly prescribed prescription-utilization regimens;

selecting one of the regimens and programming the device in accordance therewith;

activating an event switch in conjunction with a patient using the prescription corresponding to a respective prescription-utilization regimen for registering use of the prescription; and displaying prescription information to the patient, wherein the event switch causes the control step to effect the display step of the time at which a next use of the prescription is scheduled, in accordance with the regimen selected by the selecting step, and wherein at least one of the pre-programmed commonly prescribed prescription-utilization regimens corresponds to a prescription to be taken on hourly intervals up to 99 hours.

37. The method according to claim 36, wherein at least one of the plurality of pre-programmed prescription-utilization regimens causes calculation of acceptable times during which the patient is scheduled to use the prescription, and wherein the calculated times are based on the following factors:
1) a preferred time at which the patient is to make first use of the prescription;
2) a regimen specific predetermined interval of time between uses of the prescription; and
3) a regimen specific predetermined time range during which it is medically acceptable for the patient to make use of the prescription.

38. A prescription compliance device comprising:

a microcontroller;

a program memory storing data representing a plurality of pre-programmed commonly prescribed prescription-utilization regimens corresponding to a plurality of prescriptions;

a selector selecting one of the regimens and programming the device in accordance therewith, the selector including an event switch which is activated in conjunction with a patient making use of a prescription corresponding to a respective prescription-utilization regimen to register use of the prescription;

a display;

an early take mechanism configured to allow the patient to make use of the prescription before the prescription is scheduled to be used at a calculated medically acceptable time, wherein the event switch causes the microcontroller to effect the display the current time for which use of the prescription is medically acceptable, in accordance with the regimen selected by the selector.

39. A prescription compliance device comprising:

control means for controlling an operation of the prescription compliance device;

program memory means for storing data representing a plurality of pre-programmed commonly prescribed prescription-utilization regimens;

select means for selecting one of the regimens and programming the device in accordance therewith, the select means including an event switch which is activated in conjunction with a patient taking a use of a prescription corresponding to a respective prescription-utilization regimen for recording the taking of the medication;

early take means for allowing the patient to take a dose of medication before the medication is scheduled to be taken, at a medically acceptable time; and display means for displaying prescription information to the patient, wherein the event switch causing the control means to effect the display means of the time at which a next use of the prescription is scheduled, in accordance with the regimen selected by the select means.

40. A prescription compliance method, comprising the steps of:

controlling an operation of the prescription compliance device;

storing data representing a plurality of pre-programmed commonly prescribed medication-taking regimens;

selecting one of the regimens and programming the device in accordance therewith;

activating an event switch in conjunction with a patient taking a dose of a medication corresponding to a respective medication-taking regimen for recording the taking of the medication;

allowing the patient to make use of the prescription at a medically acceptable time before the prescription is scheduled to be used; and displaying prescription information to the patient, wherein the event switch causes the control step to effect the display step of the time at which a next dose of medication is scheduled to be taken, in accordance with the regimen selected by the selecting step.

\* \* \* \* \*